(12) United States Patent
Pathak et al.

(10) Patent No.: US 10,294,275 B2
(45) Date of Patent: May 21, 2019

(54) SITE-SELECTIVE FUNCTIONALIZATION OF GLYCOPEPTIDE ANTIBIOTICS

(71) Applicant: Yale University, New Haven, CT (US)

(72) Inventors: Tejaskumar P. Pathak, Boston, MA (US); Scott J. Miller, Woodbridge, CT (US)

(73) Assignee: Yale University, New Haven, CT (US)

( * ) Notice: Subject to any disclaimer, the term of this patent is extended or adjusted under 35 U.S.C. 154(b) by 106 days.

(21) Appl. No.: 14/776,336

(22) PCT Filed: Mar. 13, 2014

(86) PCT No.: PCT/US2014/026157
§ 371 (c)(1),
(2) Date: Sep. 14, 2015

(87) PCT Pub. No.: WO2014/160250
PCT Pub. Date: Oct. 2, 2014

(65) Prior Publication Data
US 2016/0039881 A1 Feb. 11, 2016

Related U.S. Application Data

(60) Provisional application No. 61/780,078, filed on Mar. 13, 2012.

(51) Int. Cl.
*A61K 38/00* (2006.01)
*C07K 9/00* (2006.01)
*C07K 1/107* (2006.01)

(52) U.S. Cl.
CPC ............ *C07K 9/001* (2013.01); *C07K 1/1077* (2013.01); *C07K 9/008* (2013.01); *A61K 38/00* (2013.01)

(58) Field of Classification Search
None
See application file for complete search history.

(56) References Cited

U.S. PATENT DOCUMENTS 5,312,738 A * 5/1994 Hamill .................... C12R 1/365
435/253.2

FOREIGN PATENT DOCUMENTS

WO  WO 98/00153  *  1/1998

OTHER PUBLICATIONS

Malnar et al (Journal of Molecular Catalysis B: Enzymatic 10, 2000, 545-549).*
Liu et al., Nat Chem Biol. May 2011;7(5):304-9.*
Malnar, etal., "Chloroperoxidase-catalyzed chlorination of didechloroaglucovancomycin and vancomycin" , J Mol Catalysis B:Enzymatic, 10(6):545-9 (2000).
Pathak, et al., "Site-selective bromination of vancomycin" , J Am Chem Soc., 134(14):6120-3 (2012).
Pathak, et al., "Chemical tailoring of teicoplanin with site-selective reactions" , J Am Chem Soc., 135(22):8415-22 (2013).
International Search report for corresponding PCT Application PCT/US2014/026157 dated Oct. 21, 2014.

* cited by examiner

*Primary Examiner* — Sergio Coffa
(74) *Attorney, Agent, or Firm* — Pabst Patent Group LLP

(57) ABSTRACT

Site-selective functionalized glycopeptide antibiotics, methods of making and using are described herein. The compounds exhibit improved activity against methicillin-susceptible *S. aureus* (MSSA), methicillin-resistant *S. aureus* (MRSA), vancomycin-sensitive *S. aureus* (VSE), vancomycin-resistant enterococci (VRE), or combinations thereof. The compounds can be administered as the neutral free acid or free base or can be administered as a pharmaceutically acceptable acid-addition or base-addition salt. The compounds can be formulated with one or more pharmaceutically acceptable excipients to prepare pharmaceutical compositions. The compounds can be administered by a variety of routes of administration including enteral, parenteral, topical, or transmucosal.

21 Claims, 10 Drawing Sheets

SITE-SELECTIVE FUNCTIONALIZATION OF GLYCOPEPTIDE ANTIBIOTICS

CROSS-REFERENCE TO RELATED APPLICATIONS

This application is a 371 application of International Application No. PCT/US2014/026157, filed Mar. 13, 2014, which claims benefit of and priority to U.S. Provisional Application No. 61/780,078, filed Mar. 13, 2013.

STATEMENT REGARDING FEDERALLY SPONSORED RESEARCH OR DEVELOPMENT

This invention was made with Government Support under Agreement NIH (GM-068649) awarded to Dr. Scott J. Miller by the National Institutes of Health. The Government has certain rights in the invention.

FIELD OF THE INVENTION

This invention is in the field of derivatives of glycopeptide antibiotics, particularly site-selectively functionalized glycopeptide antibiotics, which have activity against Gram-positive bacteria, particular vancomycin-susceptible or vancomycin-resistant bacteria.

BACKGROUND OF THE INVENTION

Glycopeptide antibiotics are a class of antibiotic drugs which include glycosylated cyclic or polycyclic nonribosomal peptides. Examples include vancomycin, teicoplanin, telavancin, bleomycin, ramoplanin, and decaplanin.

Glycopeptide antibiotics inhibit the synthesis of cell walls in susceptible microbes by inhibiting peptidoglycan synthesis. The compounds bind to the amino acids within the cell wall preventing the addition of new units to the peptidoglycan. In particular, the compounds bind to acyl-D-alanyl-D-alanine in peptidoglycan.

Due to their toxicity, use of glycopeptide antibiotics is restricted to patients who are critically ill, who have a demonstrated hypersensitivity to the β-lactams, and/or who are infected with β-lactam-resistant species. These antibiotics are effective principally against Gram-positive cocci. They exhibit a narrow spectrum of action, and are bacteriocidal only against the enterococci. Glycopeptide antibiotics continue to be one of the last effective lines of defense for cases of Methicillin-resistant *Staphylococcus aureus* (MRSA). However, vancomycin-resistant enterococci (VRE) and Vancomycin-resistant *staphylococcus aureus* (VRSA) has been seen in some countries.

There exists a need for derivatives of glycopeptide antibiotics which are effective at treating vancomycin-susceptible or vancomycin resistant enterococci or *Staphylococcus aureus*.

Therefore, it is an object of the invention to provide derivatives of glycopeptide antibiotics which are effective at treating vancomycin-susceptible or vancomycin resistant enterococci or *Staphylococcus aureus*, and methods of making and using thereof.

SUMMARY OF THE INVENTION

Site-selective functionalized glycopeptide antibiotics and methods of making and using thereof are described herein. In some embodiments, selectively functionalized derivatives of glycopeptide antibiotics, including but not limited to, vancomycin, teicoplanin, orientin C, telavancin, ristocetin, balhimycin, chloroeremomycin, avoparcin, oritavancin, and dalbavancin, are described herein. The glycopeptide to be functionalized can be naturally occurring, semi-synthetic, or synthetic. Glycopeptide antibiotics can be distinguished as having a single (5,7) biaryl functionality (vancomycin, telavancin, orientin C, chloroeremomycin, and balhimycin) or two (1,3 and 5,7) biaryl functionalities (teicoplanin, ristocetin, and delbavancin).

In one embodiment, compounds containing a single biaryl functionality contain one more substitutions on the 5,7-biaryl functionality. For example, the compound can be substituted at the $7_d$, $7_f$, and/or $7_d$ and $7_f$ positions. In other embodiments, the derivatives contain one substitution on the 5-aryl ring (e.g., $5_e$ position) and two substitutions on the 7-aryl ring ($7_d$ and $7_f$ positions). In other embodiments, the derivatives can contain one substitution on the 5-aryl ring (e.g., $5_e$ position) or $5_e$ and $7_d$ or $7_f$. The sites in question can be substituted with any functional group provided it is synthetically feasible. For example, the derivatives can be halogenated at multiple positions. After halogenation, one of the halogenated sites can be further functionalized by a cross-coupling reaction. The remaining halogens can be retained or removed by hydrogenation. Alternatively, the compounds can be functionalized after the cross-coupling reaction, e.g., halogenating already functionalized glycopeptide.

In another embodiment, compounds containing two biaryl functionalities contain one more substitutions on the 5,7-biaryl functionality. In more particular embodiments, the derivatives contain one substitution on the 7-aryl ring ($7_f$ position) or one substitution on the 3-aryl ring ($3_b$ position). In other embodiments, the derivatives contain one substitution on the 7-aryl ring ($7_f$ position) and one substitution on the 3-aryl ring ($3_b$ position). In still other embodiments, the derivatives contain one substitution on the 7-aryl ring and two substitutions on the 3-aryl ring. Other substitution patterns can also be obtained. For example, substitution patterns which are orthogonal to the patterns described above (e.g., di- or tri-functionalized derivatives with a single substitution on the 5-aryl ring) may also be obtained. The sites in question can be substituted with any functional group provided it is synthetically feasible. For example, the derivatives can be halogenated at multiple positions. After halogenation, one of the halogenated sites can be further functionalized by a cross-coupling reaction. The remaining halogens can be retained or removed by hydrogenation. Alternatively, the compounds can be functionalized after the cross-coupling reaction, e.g., halogenating already functionalized glycopeptide.

In some embodiments, the substitutions are halogens, such as Br, Cl, or I. In other embodiments, the substitutions are substituted or unsubstituted aryl or heteroaryl groups, such as phenyl groups, furan groups, and biaryl groups, optionally bridged by one or more atoms, such as carbon or heteroatoms (e.g., O, S, N, etc.), substituted or unsubstituted alkanes, alkenes, and alkynes, and substituted or unsubstituted cycloalkanes or heterocycloalkanes. The sites may also be selectively functionalized using Mannich-type reactions as well as cross-coupling alkyl (e.g., Stille or Suzuki coupling) and alkynyl (Sonogashira) groups.

In some embodiments, the compounds exhibit improved activity against methicillin-susceptible *S. aureus* (MSSA), methicillin-resistant *S. aureus* (MRSA), vancomycin-sensitive enterococci (VSE), vancomycin-resistant enterococci (VRE), and vancomycin-resistant *S. aureus* (VRSA), or combinations thereof.

The compounds can be administered as the neutral free acid or free base or can be administered as a pharmaceutically acceptable acid-addition or base-addition salt. The compounds can be formulated with one or more pharmaceutically acceptable excipients to prepare pharmaceutical compositions. The compounds can be administered by a variety of routes of administration including enteral, parenteral, topical, or transmucosal.

DETAILED DESCRIPTION OF THE INVENTION

I. Definitions

Figure 1:
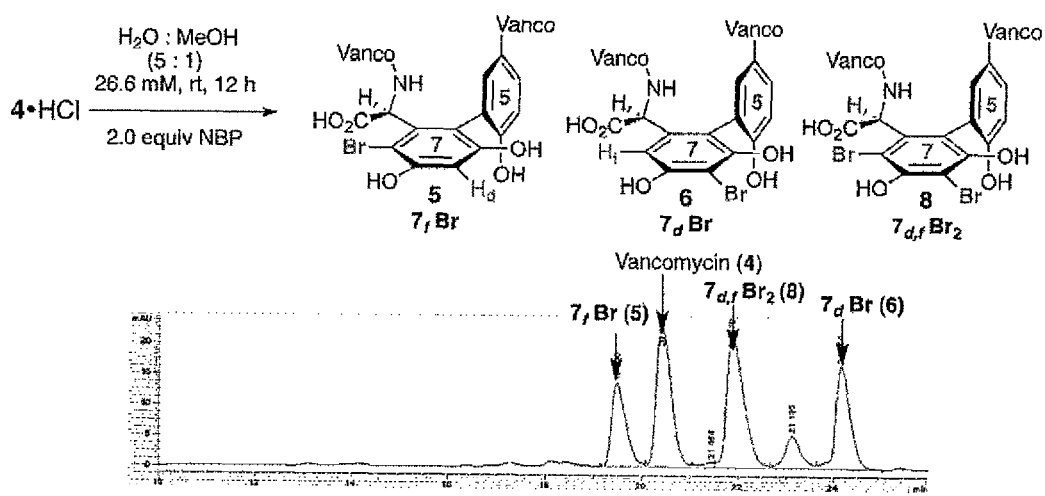
FIG. 1a is a reaction scheme showing the bromination of vancomycin hydrochloride in the absence of catalyst. As shown in the accompanying HPLC trace (FIG. 1b), the reaction provides a mixture of mono- and dibrominated products with the major product being unreacted vancomycin.

In describing and claiming the disclosed subject matter, the following terminology will be used in accordance with the definitions set forth below.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

"Site-selective functionalization" or "selectively-functionalized", as used herein, means functionalization of a specific site in a complex molecule with synthetically useable selectivity, in the presence of other sites of similar reactivity.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The alkyl groups can also be substituted with one or more groups as defined below including, but not limited to, halogen, hydroxy, amino, thio, ether, ester, carboxy, oxo, and aldehyde groups. The alkyl groups may also contain one or more heteroatoms. "Lower alkyl", as used herein, means 1-6 carbons, preferably 1-5 carbons, more preferably 1-4 carbons, most preferably 1-3 carbons.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S— alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O— alkyl, —O-alkenyl, and —O-alkynyl. Aroxy can be represented by —O-aryl or O-heteroaryl, wherein aryl and heteroaryl are as defined below. The alkoxy and phenoxyl groups can be substituted as described above for alkyl.

The terms "amine" and "amino" are art-recognized and refer to both unsubstituted and substituted amines, e.g., a moiety that can be represented by the general formula:

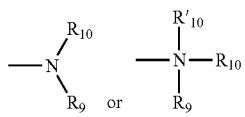

wherein, $R_9$, $R_{10}$, and $R'_{10}$ each independently represent a hydrogen, an alkyl, an alkenyl, —$(CH_2)_m$—$R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term "amine" does not encompass amides, e.g., wherein one of $R_9$ and $R_{10}$ represents a carbonyl. In even more preferred embodiments, $R_9$ and $R_{10}$ (and optionally $R'_{10}$) each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amide" is art-recognized as an amino-substituted carbonyl and includes a moiety that can be represented by the general formula:

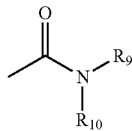

wherein, $R_9$ and $R_{10}$ are as defined above.

"Aryl" as used herein, refers to 5-, 6- and 7-membered aromatic, heterocyclic, fused aromatic, fused heterocyclic, biaromatic (e.g., biphenyl), or bihetereocyclic (e.g., bipyridinyl) ring system, optionally substituted with one or more substituents including, but not limited to, by halogen, hydroxy, nitro, cyano, amino, primary, secondary, or tertiary amino, formyl, acyl, carboxylate, alkoxy, thioether, alkyl, alkenyl, and alkynyl, cycloalkyl, etc. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Aryl" includes substituted and unsubstituted biaryl and biheteroaryl compounds, optionally interrupted or bridged by one more atoms such as carbon and/or heteroatoms (e.g., O, S, N, etc.). Examples include, but are not limited to, biaryl ethers, biaryl amines, biaryl thiols, biheteroaryl ethers, biheteroaryl amines and biheteroaryl thiols.

"Alkylaryl", as used herein, refers to an alkyl group substituted with an aryl group (e.g., an aromatic or hetero aromatic group).

The term "carbocycle", as used herein, refers to an aromatic or nonaromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $(C_{1-4})$ alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "carbonyl" is art-recognized and includes such moieties as can be represented by the general formula:

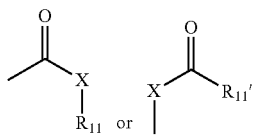

wherein, X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is a hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen; the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium. Other heteroatoms include silicon and arsenic.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Prodrug", as used herein, refers to a pharmacological substance (drug) which is administered in an inactive (or significantly less active) form. Once administered, the prodrug is metabolized in the body (in vivo) into the active compound.

The term "therapeutically effective" or "effective amount" means that the amount of the composition used is of sufficient quantity to ameliorate one or more causes or symptoms of a disease or disorder. Such amelioration only requires a reduction or alteration, not necessarily elimination. As used herein, the terms "therapeutically effective amount" "therapeutic amount" and "pharmaceutically effective amount" are synonymous. One of skill in the art can readily determine the proper therapeutic amount.

The term "patient" or "subject" to be treated refers to either a human or non-human animal.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diasteromers can be resolved or separated using techniques known in the art. "Chirality" also includes axial and planar chirality.

II. Compounds

Derivatives of glycopeptide antibiotics including, but not limited to, vancomycin, teicoplanin, orientin C, telavancin, ristocetin, balhimycin, chloroeremomycin, avoparcin, oritavancin, and dalbavancin, are described herein. These glycopeptide antibiotics can be distinguished as having a single (5,7) biaryl functionality in the core structure (vancomycin, telavancin, orienticin C, chloroeremomycin, and balhimycin) or two (1,3 and 5,7) biaryl functionalities in the core structure. In some embodiments, the derivatives are selectively functionalized at one or more positions of the 1,3-biaryl functionality and/or the 5,7-biaryl functionality. In other embodiments, the derivatives are selectively functionalized at one or more positions of the 1,3-biaryl functionality and/or the 5,7-biaryl functionality and one or more additional positions on the molecule, such as 2-ring chlorine, 6-ring chlorine, sugars, carboxylic acid and/or amine.

In one embodiment, compounds containing a single biaryl functionality contain one more substitutions on the 5,7-biaryl functionality. For example, the compound can be substituted at the $7_d$, $7_f$, and/or $7_d$ and $7_f$ positions. In other embodiments, the derivatives contain one substitution on the 5-aryl ring (e.g., $5_e$ position) and two substitutions on the 7-aryl ring ($7_d$ and $7_f$ positions). In other embodiments, the derivatives can contain one substitution on the 5-aryl ring (e.g., $5_e$ position) or $5_e$ and $7_d$ or $7_f$. For example, the derivatives can be halogenated at multiple positions. After halogenation, the one of the halogenated site can be further functionalized by a cross-coupling reaction, and the remaining halogens can be removed by hydrogenation.

In another embodiment, compounds containing two biaryl functionalities contain one more substitutions on the 5,7-biaryl functionality. In more particular embodiments, the derivatives contain one substitution on the 7-aryl ring ($7_f$ position) or one substitution on the 3-aryl ring ($3_b$ position). In other embodiments, the derivatives contain on the 7-aryl ring ($7_f$ position) and one substitution on the 3-aryl ring ($3_b$ position). In still other embodiments, the derivatives contain one substitution on the 7-aryl ring and two substitutions on the 3-aryl ring. Other substitution patterns can also be obtained. For example, substitution patterns which are orthogonal to the patterns described above (e.g., di- or tri-functionalized derivatives with a single substitution on the 5-aryl ring) may also be obtained. The derivatives can be halogenated at multiple positions. After halogenation, one of the halogenated sites can be further functionalized by a cross-coupling reaction, and the remaining halogens can be removed by hydrogenation. Alternatively, the compounds can be functionalized after the cross-coupling reaction, e.g., halogenating already functionalized glycopeptide.

In some embodiments, the substitutions are halogens, such as Br, Cl, or I. In other embodiments, the substitutions are substituted or unsubstituted aryl or heteroaryl groups, such as phenyl groups, furan groups, and biaryl groups, optionally bridged by one or more atoms, such as carbon or heteroatoms (e.g., O, S, N, etc.), substituted or unsubstituted alkanes, alkenes, and alkynes, and substituted or unsubstituted cycloalkanes or heterocycloalkanes. The sites may also be selectively functionalized using Mannich-type reactions as well as cross-coupling alkyl (e.g., Stille or Suzuki coupling) and alkynyl (Sonogashira) groups.

In some embodiments, the compounds exhibit improved activity against methicillin-susceptible *S. aureus* (MSSA), methicillin-resistant *S. aureus* (MRSA), vancomycin-sensitive enterococci (VSE), vancomycin-resistant enterococci (VRE), and vancomycin-resistant *S. aureus* (VRSA), or combinations thereof.

In some embodiments, the compound is a compound of Formula I:

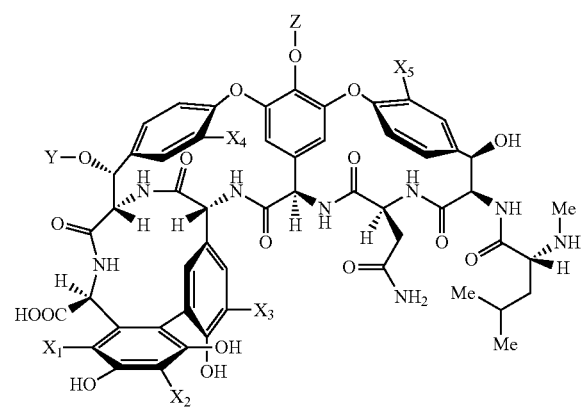

Formula I wherein each of $X_1$-$X_3$ is independently selected from hydrogen, Br, Cl, I, alkyl, substituted alkyl, cycloalkyl, substituted cycloalkyl, heterocycloalkyl, substituted heterocycloalkyl, alkenyl, substituted alkenyl, alkynyl, substituted alkynyl, aryl, substituted aryl, heteroaryl, substituted heteroaryl, amino, primary amine, or secondary, amine, alkoxy, and thioether, formyl, acyl, or carboxylic acid, $X_4$ and $X_5$ are independently selected from Br, Cl, I, alkyl, substituted alkyl, cycloalkyl, substituted cycloalkyl, heterocycloalkyl, substituted heterocycloalkyl, alkenyl, substituted alkenyl, alkynyl, substituted alkynyl, aryl, substituted aryl, heteroaryl, substituted heteroaryl, amino, primary amine, or secondary, amine, alkoxy, and thioether, formyl, acyl, or carboxylic acid, Y and Z are independently selected from hydrogen, alkyl, substituted alkyl, aryl, substituted aryl, heteroaryl, substituted heteroaryl, and carbohydrate.

In some embodiments, if $X_4$ and $X_5$ are Cl, at least one of $X_1$-$X_3$ is not hydrogen.

In some embodiments, if $X_2$ is I, $X_1$ and/or $X_3$ are other than hydrogen and/or $X_4$ and/or $X_5$ are other than Cl.

In other embodiments, $X_2$ is not (a) $CH_2NH$—$CHR_1$—$(CH_2)_m$—$NHSO_2R_4$, wherein m is 1-6 and $R_1$ is H or lower alkyl, (b) $CH_2NH$—$CHR_1$—$(CH_2)_m$—$CONHSO_2R_4$, wherein n is 0-6 and $R_1$ is H or lower alkyl, (c) $CH_2NH$—$CHR_1$—$(CH_2)_o$—$(CH_2)_p$—$NHSO_2R_4$, wherein o and p are 1-6 and $R_1$ is H or lower alkyl, (d) $CH_2NR_2$—$CHR_1$—$(CH_2)_q$$NR_3SO_2R_4$, wherein q is 2-4, $R_1$ is H or lower alkyl, $R_2$ and $R_3$ are independently hydrogen, lower alkyl or taken together represent —$CH_2$—, (e) H, (f) $CH_2NH$—$CHR_1$—$(CH_2)_m$—$NHCONHR_4$, wherein m is 1-6 and $R_1$ is H or lower alkyl, (g) $CH_2NHCH_2PO_3H_2$, (h) amino lower alkyl, wherein amino portion is further substituted with unsubstituted or substituted alkyl, alkenyl, cycloalkyl, cycloalkenyl, arylaryl, alkoxy, aryloxy, substituted alkoxy, and substituted aryloxy, (i) $CH_2NH$—$CHR_1$—$(CH_2)_n$—$NHCOR_4$, wherein n is 0-6 and $R_1$ is H or lower alkyl, (j) $CH_2NH$—$CHR_1$—$(CH_2)_n$—$CONHR_4$, wherein n is 0-6 and $R_1$ is H or lower alkyl, (k) $CH_2NH$—$CHR_1$—$(CH_2)_o$—O—$(CH_2)_p$N-$HCOR_4$, wherein o and p are 1-6 and $R_1$ is H or lower alkyl, or (l) optionally substituted alkyl, which may be interrupted by a heteroatom-containing group, wherein $R_A$ is aryl, $C_1$-$C_{12}$-alkyl, $C_1$-$C_{12}$-alkyl substituted with one or more substituents selected from the group consisting of halogen, hydroxy, $C_1$-$C_{12}$-alkoxy, $C_1$-$C_3$-alkoxy-$C_1$-$C_3$-alkoxy, amino, $C_1$-$C_{12}$-alkylamino, $C_1$-$C_{12}$-dialkylamino, alkenyl, alkynyl, and $C_1$-$C_{12}$-thioalkoxy, $C_1$-$C_{12}$-alkyl substituted with aryl, $C_1$-$C_{12}$-alkyl substituted with substituted aryl, $C_1$-$C_{12}$-alkyl substituted with heteroaryl, $C_1$-$C_{12}$-alkyl substituted with substituted heteroaryl, cycloalkyl, heteroaryl, heterocycloalkyl, aryl substituted with one or more substituents selected from the group consisting of halogen, hydroxy, $C_1$-$C_{12}$-alkoxy, $C_1$-$C_{12}$-alkoxy-$C_1$-$C_{12}$-alkoxy, amino, amino-$C_1$-$C_{12}$-alkoxy, $C_1$-$C_{12}$-alkylamino, $C_1$-$C_{12}$-alkylamino-$C_1$-$C_{12}$-alkoxy, $C_1$-$C_{12}$-dialkylamino, $C_1$-$C_{12}$-dialkylamino-$C_1$-$C_{12}$-alkoxy, alkenyl, alkynyl, $C_1$-$C_{12}$-thioalkoxy, $C_1$-$C_{12}$-alkyl, $C_1$-$C_{12}$-substituted alkyl, $C_1$-$C_{12}$-alkoxy-morpholino, $C_1$-$C_{12}$-alkoxy-$C_1$-$C_{12}$-dialkoxyamino, $C_1$-$C_{12}$-alkoxy-$NHSO_2C_1$-$C_6$alkyl, and $C_1$-$C_{12}$-alkoxy-$NHCOC_1$-$C_6$alkyl, or heteroaryl substituted with one or more substituents selected from the group consisting of halogen, hydroxy, CpCn-alkoxy, $C_1$-$C_{12}$-alkoxy-$C_1$-$C_{12}$-alkoxy, amino, amino-$C_1$-$C_{12}$-alkoxy, $C_1$-$C_{12}$-alkylamino, $C_1$-$C_{12}$-alkylamino-$C_1$-$C_{12}$-alkoxy, $C_1$-$C_{12}$-dialkylamino, $C_1$-$C_{12}$-dialkylamino-$C_1$-$C_{12}$-alkoxy, alkenyl, alkynyl, $C_1$-$C_{12}$-thioalkoxy, $C_1$-$C_{12}$-alkyl, and $C_1$-$C_{12}$-substituted alkyl; or if $X_2$ is one of (a)-(l), then $X_1$ and/or $X_3$ is other than hydrogen and/or $X_5$ and/or $X_6$ is other than Cl.

In some embodiments, the compound is as described above, wherein Y is hydrogen or a carbohydrate. Suitable carbohydrates include, but are not limited to, N-acylglucosamine, a glucosamine, or an oxoglucosamine. Other carbohydrates can be introduced using chemistry (e.g., enzyme catalysis) known in the art.

In some embodiments, the compound is as described above including Y, wherein Z is a carbohydrate including, but not limited to, an arabinohexopyranose. In particular embodiments, the arabinohexopyranose is substituted with 4'-chlorobiphenylmethyl. Other carbohydrates can be introduced using chemistry (e.g., enzyme catalysis) known in the art.

In some embodiments, the core molecule is vancomycin, orientin C, chloroeremomycin, balhimycin, or telavancin or these molecules without the carbohydrate moieties.

In some embodiments, $X_1$ is a halogen, such as Br, Cl or I and $X_2$ and $X_3$ are hydrogen. In other embodiments, $X_2$ is a halogen, such as Br, Cl or I and $X_1$ and $X_3$ are hydrogen. In other embodiments, $X_{1-3}$ are halogen, such as Br, Cl, or I. The halogenated compounds can serve as substrates for metal-catalyzed coupling reactions, such as Suzuki coupling, to introduce substituted or unsubstituted alkyl, cycloalkyl, aryl, or heteroaryl groups onto the molecule.

In other embodiments, the compound is a compound of formula II:

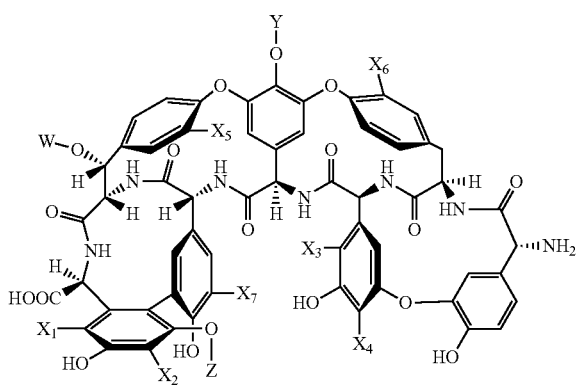

Formula II wherein:

each of $X_1$-$X_4$ and $X_7$ is independently selected from the group consisting of hydrogen, Br, Cl, I, alkyl, substituted alkyl, cycloalkyl, substituted cycloalkyl, heterocycloalkyl, substituted heterocycloalkyl, alkenyl, substituted alkenyl, alkynyl, substituted alkynyl, aryl, substituted aryl, heteroaryl, substituted heteroaryl, amino, primary amine, or secondary, amine, alkoxy, thioether, formyl, acyl, or carboxylic acid, $X_5$ and $X_6$ are independently selected from the group consisting of hydrogen, Br, Cl, I, alkyl, substituted alkyl, cycloalkyl, substituted cycloalkyl, heterocycloalkyl, substituted heterocycloalkyl, alkenyl, substituted alkenyl, alkynyl, substituted alkynyl, aryl, substituted aryl, heteroaryl, substituted heteroaryl, amino, primary amine, or secondary, amine, alkoxy, thioether, formyl, acyl, or carboxylic acid, wherein if $X_5$ and $X_6$ are Cl, at least one of $X_1$-$X_4$ and $X_7$ is not hydrogen, W, Y, and Z are independently selected from the group consisting of hydrogen, alkyl, substituted alkyl, aryl, substituted aryl, heteroaryl, substituted heteroaryl, and carbohydrate.

In some embodiments, the compound is as described above and W is hydrogen or N-acetylglucosamine, Z is hydrogen or alpha-D-mannose, and/or Y is hydrogen or a substituted beta-D-glucosamine having the structure:

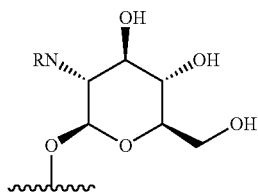

wherein R is an acyl (R—(C=O)—) group.

In some embodiments, R is selected from 4-decenoyl ($A_2$-1), 9-methylnonanoyl ($A_2$-2), decanoyl ($A_2$-3), 8-methyldecanoyl ($A_2$-4), 9-methyldecanoyl ($A_2$-5).

In some embodiments, one or more of $X_1$-$X_4$ is Br, Cl, or I. In some embodiments, $X_1$ is a halogen, such as Br, Cl, or I and $X_{2-4}$ are hydrogen. In other embodiments, $X_3$ is a halogen, such as Br, Cl, or I and $X_1$, $X_2$, and $X_4$ are hydrogen. In other embodiments, $X_1$ and $X_3$ are halogen, such as Br, Cl, or I and $X_2$ and $X_4$ are hydrogen. In other embodiments, $X_2$, $X_3$, and $X_4$ are halogen, such as Br, Cl, or I and $X_1$ is hydrogen. Other substitution patterns can also be obtained. For example, substitution patterns which are orthogonal to the patterns described above (e.g., di- or tri-functionalized derivatives with a single substitution on the 5-aryl ring) may also be obtained.

The halogenated compounds can serve as substrates for metal-catalyzed coupling reactions, such as Suzuki coupling, to introduce substituted or unsubstituted alkyl, alkenyl, alkynyl, cycloalkyl, heterocycloalkyl, aryl, or heteroaryl groups. In some embodiments, wherein $X_1$-$X_4$ is Br, Cl, or I, $X_5$ and/or $X_6$ is substituted or unsubstituted aryl, such as 3-furyl. In other embodiments, $X_1$, $X_2$, and $X_4$ are hydrogen, $X_3$ is 3-furyl, and $X_5$ and $X_6$ are chlorine. In other embodiments, $X_1$, $X_2$, and $X_4$ are hydrogen, $X_3$ is 3-furyl, and $X_5$ is chlorine. In still other embodiments, $X_1$ is Br, $X_2$-$X_4$ are hydrogen, $X_5$ is Cl, and $X_6$ is 3-furyl.

In some embodiments, $X_1$ is Br, $X_2$-$X_4$ are hydrogen, $X_5$ is Cl, and $X_6$ is substituted or unsubstituted biphenyl, biphenyl ether, biphenyl thioether, or biphenyl amine. In other embodiments, $X_1$-$X_4$ are hydrogen, $X_5$ is Cl, and $X_6$ is substituted or unsubstituted biphenyl, biphenyl ether, biphenyl thioether, or biphenyl amine.

In some embodiments, $X_1$-$X_4$ are as described above and $X_5$ and/or $X_6$ is alkyl or alkenyl. In particular embodiments, $X_1$-$X_4$ are hydrogen, $X_5$ is Cl, and $X_6$ is 1-octenyl.

In some embodiments, if the core compound is ristocetin and $X_3$ is I, than $X_1$ and/or $X_2$ are other than hydrogen and/or $X_5$ and/or $X_6$ are other than chlorine.

In still other embodiments, the compound is a compound of Formula III:

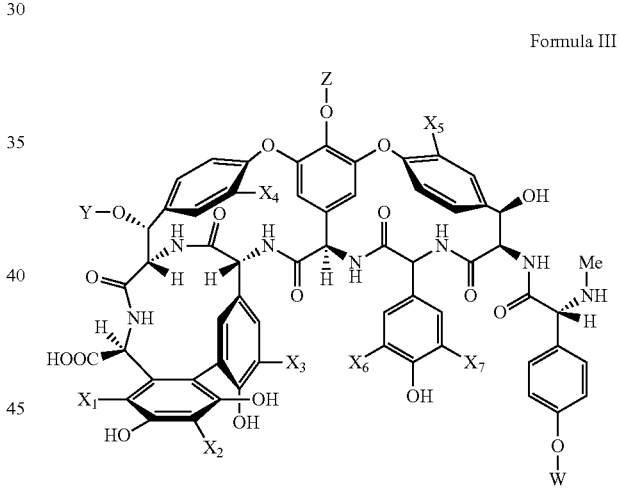

Formula III wherein:

each of $X_1$-$X_3$, $X_6$, and $X_7$ is independently selected from the group consisting of hydrogen, Br, Cl, I, alkyl, substituted alkyl, cycloalkyl, substituted cycloalkyl, heterocycloalkyl, substituted heterocycloalkyl, alkenyl, substituted alkenyl, alkynyl, substituted alkynyl, aryl, substituted aryl, heteroaryl, substituted heteroaryl, amino, primary amine, or secondary, amine, alkoxy, thioether, formyl, acyl, or carboxylic acid, $X_4$ and $X_5$ are independently selected from the group consisting of hydrogen, Br, Cl, I, alkyl, substituted alkyl, cycloalkyl, substituted cycloalkyl, heterocycloalkyl, substituted heterocycloalkyl, alkenyl, substituted alkenyl, alkynyl, substituted alkynyl, aryl, substituted aryl, heteroaryl, substituted heteroaryl, amino, primary amine, or secondary, amine, alkoxy, thioether, formyl, acyl, or carboxylic acid, wherein if $X_4$ and $X_5$ are Cl, at least one of $X_1$-$X_3$, $X_6$, and $X_7$ is not hydrogen, W, Y, and Z are independently selected from the group consisting of hydrogen, alkyl, substituted alkyl, aryl, substituted aryl, heteroaryl, substituted heteroaryl, and carbohydrate.

In some embodiments, W, Y, and Z are carbohydrates.

In some embodiments, the compound is as described above and one or more of $X_1$-$X_3$ is Br, Cl, or I. In other embodiments, $X_3$ and/or $X_6$ is aryl.

III. Formulations

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

A. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

1. Controlled Release Formulations

The parenteral formulations described herein can be formulated for controlled release including immediate release, delayed release, extended release, pulsatile release, and combinations thereof.

i. Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug-containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

In certain embodiments, it may be desirable to provide continuous delivery of one or more compounds to a patient in need thereof. For intravenous or intraarterial routes, this can be accomplished using drip systems, such as by intravenous administration. For topical applications, repeated application can be done or a patch can be used to provide continuous administration of the compounds over an extended period of time.

2. Injectable/Implantable Solid Implants

The compounds described herein can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

i. Controlled Release Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

C. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, and combination thereof.

1. Topical Formulations

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof; DMSO and related compounds, ionic compounds, azone and related compounds, and solvents, such as alcohols, ketones, amides, polyols (e.g., glycols). Examples of these classes are known in the art.

i. Lotions, Creams, Gels, Ointments, Emulsions, and Foams

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases, which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, it may be desirable to provide continuous delivery of one or more compounds to a patient in need thereof. For topical applications, repeated application can be done or a patch can be used to provide continuous administration of the compounds over an extended period of time.

D. Pulmonary Formulations

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

IV. Methods of Making Glycopeptide Derivatives

Synthesis of analogs of glycopeptide antibiotics, such as vancomycin and teicoplanin, for biological evaluation continues to attract research interest. The enhanced complexity of teicoplanin renders direct and selective functionalization of more challenging than the related goal of direct functionalization of vancomycin. Also, whereas vancomycin is readily available in homogeneous form through a fermentation process, teicoplanin is obtained as a complex mixture. Further purification is therefore necessary to obtain a homogeneous starting material for study of selective chemical reactions.

A. Site Selective Halogenation of Vancomycin

1. Halogenation in Absence of Peptide Catalysts

Exposure of vancomycin (4) to 2.0 equiv of NBP produced a mixture of products (5, 6, and 8), with unreacted vancomycin as a major component. LC-MS analysis and extensive preparative HPLC purification allowed for isolation of the major constituents albeit in modest quantities. The uncatalyzed bromination of vancomycin produced an essentially 1:1 ratio of the monobromovancomycins $7_f$-Br (5) and $7_d$-Br (6) along with a very similar quantity of the dibromovancomycin $7_{d,f}$-Br (8) (see FIG. 1).

2. Halogenation in Presence of Peptide Catalyst

Given the well-known binding of vancomycin to DAla-DAla segments of the bacterial cell wall as part of its biological mode of action, catalysts were designed based on this molecular recognition motif. In particular, catalysts that retained the DXaa-DXaa dipeptide motif as part of a binding domain between the catalyst and the substrate were investigated. In addition, an N,N-dimethylamide functionality, which was anticipated to accelerate the bromination reactions, was incorporated into the peptide catalyst.

A series of 11 catalysts were evaluated at different concentrations and/or reaction times. The uncatalyzed reaction delivers essentially equal quantities of 7-Br and $7_d$-Br. N,N-dimethylacetamide itself as a promoter provided neither a noticeable rate acceleration nor a significant change in the $7_f$-Br/$7_d$-Br ratio, although slightly more of the dibromo compound was observed.

When peptides containing the DAla-DAla sequence along with the N,N-dimethylamido side chain were used, essentially all of the starting material (4) was consumed within 2 h. This is significant faster that the rate of consumption of vancomycin in the control experiments. Moreover, the product distribution responded to structural changes in the peptide. For example, peptide 10, with a Asn(Me2)-DAla-DAla structure, gave the 7d-Br (6) compound as the major product with a 6.8:1 preference over monobromide 7f-Br (5), with the dibromide (8) also formed in considerable quantity.

Altering the stereochemistry of the DAsn(Me2) residue (peptide 11) also delivered 7d-Br (6) as the major product, but with a lower 7d-Br/7f-Br ratio (4.9:1). It was also observed that exchange of the Asn residue to Gln(Me2) (catalyst 12) also contributed to efficient consumption of (4), with the dibromide (8) emerging as the dominant product of the reaction. When the N,N-dimethylamide moiety was excised from the peptide structure (peptide 14), much lower conversion was observed. However, a preference for 7d-Br (6) was still observed.

The peptide concentration and stoichiometry influence substantially both the rate and product distribution. Lowering the concentration led to a significant improvement in the 6:5 ratio (14.6:1) without an appreciable rate decrease. Increasing the peptide loading to 200 mol % led to a modest improvement in the 6:5 ratio (19:1). On the other hand, lowering the peptide loading to 50 mol % gave a lower 6:5 ratio (3.4:1). 50 mol % peptide resulted in full consumption of 4 within 2 h. However, reduction of the peptide loading to 25 mol % led to a further erosion of the selectivity relative to the results observed with higher peptide amounts (1.9:1.0). These results imply that while the peptide-based promoters exhibit rate acceleration, a principal hallmark of catalysis, the turnover rates do not appear to be high in the present case. This latter phenomenon may be due to the high affinity of 4 for the DAla-DAla motif.

The effect of relocating the Asn(Me2) residue within the tripeptide also influenced both the rate and product distribution. When the residue was disposed closer to the C-terminal position, the peptide appeared to be a less effective promoter, as the rate diminished and the selectivity for 6 decreased. These observations may reveal the importance of situating the directing functional group at the right location. Finally, when a limiting quantity (0.5 equiv) of NBP is used, the selectivity trends were preserved and the quantity of dibromide 8 was reduced. The observations in these two experiments suggest that the preference for monobromide 6 is not simply a function of overconversion and depletion of 5.

Based on the results, peptide 10 was explored for preparative reactions of particular brominated vancomycins. Under the optimized reaction conditions, treatment of 100 mg of 4 provided 43.1 mg (41% yield) of analytically pure 7d-Br derivative 6 in a single experiment. By way of comparison, 100 mg of 4 under the uncatalyzed reaction conditions delivered only 11.6 mg (11% yield) of 6 and a tedious purification was required to isolate 6.

The synthesis of dibromovancomycin 8 was also investigated. This particular derivative is generally the major product in the uncatalyzed bromination of 4 with excess brominating reagent. However, as noted, these reactions are generally unselective, which makes product isolation difficult. On the other hand, treatment of 4 with NBP (3 equiv) in the presence of 100 mol % 10 provides the desired product with excellent efficiency. The treatment of 100 mg of 4 under peptide-promoted reaction conditions provided 60.2 mg (55% yield) of analytically pure 8 in a single experiment.

Treatment of 4 with NBP in the presence of 100 mol % 10 under otherwise identical conditions enabled the observation of 8 and 17, although with ratios no better than ~1:1. Characterization of 17 allowed its assignment as the illustrated tribromovancomycin, wherein the phenolic moiety of residue 5 was also brominated. When 4 was exposed to NBP under the reaction conditions in the presence of catalyst 18, tribromide 17 was produced in significant quantity preferentially over the dibromide (17:8=3-4:1) in a substantially cleaner reaction. In a preparative experiment, 49.0 mg of 4 led to the isolation of 20.2 mg (35% yield) of 17. This observation demonstrates the power of a peptide catalyst to provide a new brominated vancomycin that is otherwise difficult to acquire.

A preliminary examination of DAla-DAla-based peptides did not unveil a 5-selective catalyst. However, it was observed that the reaction medium had a substantial effect on the site-selectivity of the initial bromination. When 4 is exposed to 2 equiv of NBP in either $H_2O$:MeOH (5:1) or MeOH alone, sluggish reactions occur, and the ratio of 5:6 is near unity. Yet, when a larger quantity (4 equiv of NBP) is employed, in the absence of a catalyst, an unexpected preference for 5 is observed, with a substantial increase in the observed quantity of dibromide 8. Peptide 10 maintains its capacity to favor 6 in MeOH solvent, although the selectivity is strongly attenuated.

Guanidine was investigated as an additive because of its propensity to accelerate bromination reactions. Additionally, guanidine possesses the capacity to bind carboxylate under a variety of conditions. Guanidine not only provided 5 with good selectivity over 6 but also significantly improves the ratio of monobromide (5) to dibromide (8), making viable the isolation of 5 in good quantities. On a preparative scale, the reaction of 100 mg of 4 with 4 equiv of NBP in the presence of guanidine provided 23.3 mg (21% yield) of analytically pure 5, which is otherwise very difficult to isolate cleanly in significant quantities. These results are consistent with the hypothesis that guanidine may associate with the acid of 4 and simultaneously deliver the bromide ion. This effect may lead to kinetically favored formation of 5 and also the formation of 8 via depletion of 6.

The reactions described herein allow one to site-selectively functionalize complex molecules, such as glycopeptide antibiotics. In some embodiments, the glycopeptide contains a single biaryl functionality and the ratio of substitution at the $7_d$ position and the $7_f$ position is at least 3:1, 4; 1, 5:1, 6:1, 7:1, 8:1, 9:1, 10; 1, 11:1, 12:1, 13:1, 14:1, 15:1, 16:1, 17:1, 18:1, or 19:1. In other embodiments, the glycopeptide contains a single biaryl functionality and the ratio of substitution at the $7_f$ position and the $7_d$ position is at least 3:1, 4; 1, 5:1, 6:1, 7:1, 8:1, 9:1, 10; 1, 11:1, 12:1, 13:1, 14:1, or 15:1. In still other embodiments, the glycopeptide contains a single biaryl functionality and the ratio of substitution at the $7_{d,f}$ position and the $7_f$ or $7_d$ position is at least 3:1, 4; 1, 5:1, 6:1, 7:1, 8:1, 9:1, 10; 1, 11:1, 12:1, 13:1, 14:1, 15:1, 16:1, 17:1, 18:1, 19:1, or 20:1. In still other embodiments, the glycopeptide contains a single biaryl functionality and the ratio of substitution at the $7_{d,f}$ and $5_e$ positions (trisubstituted) and the $7_{f,d}$ positions is at least 3:1, 4; 1, 5:1, 6:1, 7:1, 8:1, 9:1, 10; 1, 11:1, 12:1, 13:1, 14:1, or 15:1.

B. Site Selective Halogenation of Teicoplanin

The structure of teicoplanin presents an additional challenge compared to vancomycin: tuning the site of bromination to either the 5,7-biaryl region of the structure or the 1,3-biaryl-ether region.

1. Halogenation in the Absence of Peptide Catalyst

Teicoplanin $A_2$-2 (3) was isolated and purified from the readily available mixture of teicoplanins, which is a composite of approximately six to nine molecular forms of teicoplanin. Studies of the site-selective bromination of $A_2$-2 (3) began with its reaction in the presence of various quantities of N-bromophthalimide (NBP). When $A_2$-2 (3) was dissolved in MeOH/$H_2O$ (1:1), and 1 equiv of NBP was employed, a single major product was observed, with unreacted $A_2$-2 (3) also prominent in the HPLC trace. When multiple equivalents were employed, a highly complex mixture of products was observed. The reaction with 1 equiv. allowed for isolation and purification of the major brominated species, $7_f$-Br (4).

2. Halogenation in the Presence of Peptide Catalysts

Teicoplanin was initially reacted with catalysts like 5, as described above for vancomycin, designed to mimic the binding of vancomycin and teicoplanin to their biological target, but outfitted with functional groups that might accelerate brominaton. When 3 was exposed to bromination conditions in the presence of peptide 5, bromination was observed, but the analytical HPLC trace exhibited broad peaks. The peak shape rendered analysis of reaction mixture and isolation of pure materials difficult. The peak shapes were attributed to the formation of robust (i.e., too robust) 3-peptide complexes. This assertion is consistent with the known, very high affinity of 3 for DAla-DAla-based peptides (Ka=1.6×106 for Ac-Lys-DAla-DAla at pH=5.0).

In an attempt to overcome the formation of these complexes, one of the DAla units was replaced with a DLeu. The corresponding bromination of 3 with Boc-Asn(Me)2-DLeu-DAla-OH (6) as a promoter of the reaction produces a reaction mixture that was readily analyzed by HPLC/LC-MS. Peptide 6 diverted the reaction to give a new mono-brominated teicoplanin, which was not observed in significant quantities in the absence of 6. The structure of the new, 6-dependent mono-brominated teicoplanin was assigned as the ring 3b-Br analog 7. The capacity of peptide 6 to re-direct the site of bromination away from the intrinsically more reactive 5,7-ring system to the less reactive 1,3-ring system is a manifestation of nonenzymatic control of site-selectivity in a highly complex molecular environment. The reaction specificity is also highly dependent on peptide structure and stereochemistry. Alteration of the configuration of the DLeu residue of the peptide to the L configuration, as in 9 (Boc-Asn(Me)2-Leu-DAla-OH), produced a very different result. In this case, the major product was the 7f-Br compound 4.

Pronounced peptide-dependent effects were also observed in the bromination of teicoplanin A2-2. When 3 was exposed to an excess of NBP (3.3 equiv), either in the absence or in the presence of different peptides (6, 10 and 11, with variable location of the Asn(Me)2 side chain) different product distributions were obtained. In the absence of a peptide-based promoter, a highly complex mixture of products was obtained. When a peptide bearing the N-terminal Asn(Me)2 side chain was employed (6), the reaction mixture contained a number of products, including a prominent HPLC peak that contains an inseparable mixture of di- and tribromides. When the Asn(Me)2 is central to the tripeptide (10), two peaks were observed in the HPLC trace that once again contain mixtures. Yet, when the Asn(Me)2 is in the C-terminal position (11), a peptide-dependent outcome was observed, with new homogeneous peaks apparent in the HPLC trace. LC-MS analysis revealed the compound to be a new tribrominated species.

The reactions described herein allow one to site-selectively functionalize complex molecules, such as glycopeptide antibiotics. In some embodiments, the glycopeptide contains two biaryl functionalities and the ratio of substitution at the $3_b$ position and the $7_f$ position is at least 3:1, 4; 1, 5:1, 6:1, 7:1, 8:1, 9:1, or 10; 1. In other embodiments, the glycopeptide contains two biaryl functionalities and the ratio of substitution at the $7_f$ position and the $3_b$ position is at least 3:1, 4; 1, 5:1, 6:1, 7:1, 8:1, 9:1, or 10; 1. In still other embodiments, the glycopeptide contains two aryl functionalities and the ratio of substitution at the $3_{b,d}$ $7_f$ positions to the mono- or dibromo compounds is at least 3:1, 4; 1, 5:1, 6:1, 7:1, 8:1, 9:1, or 10; 1.

Metal-Catalyzed Coupling Reactions

A variety of coupling reactions are known in the art wherein the substrate is an alkyl or aryl halide. Examples of such reactions include the Wurtz reaction, Ullmann reaction, Castro-Stephens coupling, Gilman coupling, Cassar reaction, Kumada coupling, Heck reaction, Sonogashira coupling, Negishi coupling, Stille cross-coupling, Suzuki coupling, Hiyama coupling, and Buchwald-Hartwig reaction.

Metal-catalyzed coupling reactions involving the C—Cl bond on amino acid residues 2 and 6 in vancomycin have been described in the literature. Vancomycin has poor solubility in organic solvent but is highly soluble in water. The reaction involved a water-soluble catalyst combination containing the water-soluble phosphine ligand sodium 2-dicylohexylphosphino-2',6'-dimethoxybiphenyl-3'-sulfonate and trans-(4-biphenyl)vinylboronic acid as the coupling agent. While the boronic acid was found to have low reactivity towards vancomycin, those that did react did so with good selectivity.

The brominated variants of teicoplanin were investigated as substrates for metal-catalyzed cross-coupling reactions, particularly Suzuki cross-coupling. Poor results were initially obtained due to the apparent binding of Pd reagents to teicoplanin that resulted in inhibition of catalysis. However, the use of higher loadings of Pd (50 mol %) along with the water-soluble phosphine ligand 13 (100 mol %) allowed cross-coupling to occur with useful efficiencies. For example, when bromoteicoplanin 7 was subjected to these conditions, furan-containing teicoplanin analog 14 was obtained in 28% yield, in a single step, with high purity after reverse phase HPLC purification. Analysis of the reaction mixture prior to purification by LC-MS revealed the presence of a minor, doubly functionalized product with two furyl groups, and possessing only a chlorine atom, suggesting functionalization of one of the indigenous chlorines of 3. This compound was assigned as 15, and was isolated in 35% yield under conditions optimized for its formation. Bromoteicoplanin 4, under analogous conditions, may be converted to compound 16 or 17, where substitution of the typically less reactive (towards metal-catalyzed cross-coupling) C—Cl bond has occurred, rather than at the generally more reactive C—Br bond. The unexpected high reactivity of the ring 2c position of 3 was the basis for the investigation of the Pd-catalyzed cross coupling of native 3 under related conditions. Compounds 18, 19 and 20 were obtained in 43%, 30% and 20% isolated yield, respectively.

V. Methods of Using Glycopeptide Derivatives

The compounds described herein can be used as antibiotics, particular against gram-positive bacteria. Vancomycin has an in vitro MIC of 0.25-10 µg/ml against *Staphylococcus aureus*. Teicoplanin exhibits antibacterial activity similar to that of vancomycin.

Vancomycin and the related glycopeptide antibiotics are indicated for the treatment of serious, life-threatening infections by Gram-positive bacteria that are unresponsive to other less-toxic antibiotics. The increasing emergence of vancomycin-resistant enterococci has resulted in the development of guidelines for use by the Centers for Disease Control (CDC) Hospital Infection Control Practices Advisory Committee. These guidelines restrict use of vancomycin to the following indications:

Treatment of serious infections caused by susceptible organisms resistant to penicillins (methicillin-resistant *Staphylococcus aureus* and multi-resistant *Staphylococcus epidermidis* (MRSE)) or in individuals with serious allergy to penicillins.

Treatment of Pseudomembranous colitis caused by the bacterium *Clostridium difficile*; in particular, in cases of relapse or where the infection is unresponsive to metronidazole treatment (for this indication, vancomycin is given orally, rather than via its typical, I.V. route).

For treatment of infections caused by gram-positive microorganisms in patients with serious allergies to beta-lactam antimicrobials.

Antibacterial prophylaxis for endocarditis following certain procedures in penicillin-hypersensitive individuals at high risk.

Surgical prophylaxis for major procedures involving implantation of prostheses in institutions with a high rate of MRSA or MRSE.

Early in treatment as an empiric antibiotic for possible MRSA infection while waiting for culture identification of the infecting organism.

While vancomycin continues to be a last line of defense, human cases of vancomycin resistant enterococci (VRE) and vancomycin resistant *Staphylococcus aureus* (VRSA) has motivated research into the development of derivatives that can effectively treat these resistant strains.

In some embodiments, the derivatives described herein have an MIC: (a) equal to or less than 0.5 µg/ml, preferably less than 0.5 µg/ml, more preferably less than 0.4 µg/ml, most preferably less than 0.3 µg/ml, such as 0.25 µg/ml against methicillin-susceptible *S. aureus* (MSSA); (b) equal to or less than 1.0 µg/ml, preferably less than 1.0 µg/ml, preferably less than 0.5 µg/ml, more preferably less than 0.4 µg/ml, most preferably less than 0.3 µg/ml, such as 0.25 µg/ml against methicillin-resistant *S. aureus* (MRSA); (c) equal to or less than 1.0 µg/ml, preferably less than 1.0 µg/ml, preferably less than 0.5 µg/ml, more preferably less than 0.4 µg/ml, more preferably less than 0.3 µg/ml, most preferably less than 0.2 µg/ml, such as 0.12 µg/ml against vancomycin-susceptible enterococci (VSE); (d) up to about 1 µg/ml against vancomycin-resistant enterococci (VRE, VanA) and 0.12 µg/ml against vancomycin-resistant enterococci (VRE, VanB).

Brominated teicoplanin and teicoplanin functionalized via Suzuki coupling were evaluated against 5 bacterial strains including methicillin-resistant *S. aureus* (MRSA) and vancomycin-resistant *enterococcus* (VRE; VanB exhibits vancomycin resistance, but it is teicoplanin susceptible; VanA is both vancomycin and teicoplanin resistant).

In comparison to control compounds, analogs 4, 7 and 8 (entries 4-6) were quite similar in potency to 3 against all five bacterial strains. In contrast, tribrominated teicoplanin A2-2 (12) exhibited a decrease in activity with four of the five strains. On the other hand, the analogs obtained through cross-coupling demonstrated comparable or increased potency against several of the bacterial strains, in comparison to vancomycin and teicoplanin. Compound 14, for example, with furyl substitution at the 3b-position, exhibited higher potency against the MRSA strain). Relocation of the furyl substituent from the 3b-position to the 2c position (compound 18) resulted in enhancement of activity against VRE strains. Compound 15), with both 2c- and 3b-positions substituted with a furyl group, exhibits a similar activity profile in comparison to 14 and 18. Compound 16 possessing the 7f-bromine substituent and the 2c-furyl group also exhibited an analogous profile. A striking and different profile was observed with compounds 17, 19 and 20. Substitution of the 2c-position of 3 with biphenyl functionality (compound 19) resulted in significant activity against VRE (VanA) strain. Simultaneously, however, compound 19 exhibited a loss of potency when evaluated against MSSA and MRSA strains. Compound 17, with a 7f-Br and a 2c-biphenyl functionality, also exhibited this trend. Compound 20, with ring 2c-octenyl substitution, exhibited the trend as well, while showing quite high (significant) potency against both vancorncin- and teicoplanin-resistant strain (Van A). These data are compared to antibacterial behaviors of the antibiotic Linezolid in entry 15. The unique behaviors of biphenyl-containing compounds 17, 19 and 20 may indicate an alternative mechanism of action.

The compounds described herein can be used to treat the same indications as vancomycin and related glycopeptide antibiotics. The appropriate dosage can be determined by the prescribing physician and is dependent on a variety of factors including age and weight of the patient, disorder to be treated, etc.

VI. Kits

The compounds described herein can be packaged in a container, such as a blister pack or bottle for commercial sale. The compounds can include prescribing information directing the administrator or patient how to administer the compound.

EXAMPLES

Example 1. Halogenation of Vancomycin

Halogenation in Absence of Catalyst

The hydrochloride salt of vancomycin (4) was reacted with 2.0 equiv. of N-bromophthalimide (NBP) at room temperature for 12 hours in water:methanol (5:1) to form a mixture of products, of which unreacted vancomycin was a major component. Additional products included 7f-Br vancomycin (5), 6d-Br vancomycin (6), and 7d,f-Br vancomycin (8). The structures and HPLC trace are shown in FIG. 1.

Halogenation in the Presence of Peptide Catalysts

Given the well-known binding of vancomycin (4) to DAla-DAla (FIG. 2) segments of the bacterial cell wall as part of its biological mode of action, a series of peptide catalysts were designed based on this molecular recognition motif. The catalysts retained the DXaa-DXaa dipeptide motif as part of a binding domain between the catalyst and the substrate. In addition, N,N-dimethylamide functionality, which was predicted to accelerate the bromination reactions, was incorporated into the catalysts. The catalysts which were investigated are shown in Table 1. All reactions were conducted in water.

TABLE 1

Optimization of Peptide Scaffold and Reaction Conditions for the conversion of 4•HCl to 5, 6 and 8[a]

| Entry | Catalyst | mol % | t (h) | % conv. | 5 6 8 $7_cBr:7_dBr:7_{d,d}Br_2$ |
|---|---|---|---|---|---|
| 1 | No catalyst | NA | 12 | 71 | 1.0:1.0:1.3[b] |
| 2a | N,N-dimethylacetamide | 100 | 12 | 68 | 1.0:1.0:1.8[b] |
| 2b | N,N-dimethylacetamide | 7100 | 16 | 64 | 1.0:1.5:2.9[b] |
| 3 | Boc-Asn(Me$_2$)-DAla-DAla-OH (10) | 100 | 2 | 97 | 1.0:6.6:2.6[b] |
| 4 | Boc-DAsn(Me$_2$)-DAla-DAla-OH (11) | 100 | 2 | 90 | 1.0:4.9:1.8[b] |
| 5 | Boc-Gln(Me$_2$)-DAla-DAla-OH (12) | 100 | 2 | 99 | 1.0:4.0:9.3[b] |
| 6 | Boc-DGln(Me$_2$)-DAla-DAla-OH (13) | 100 | 2 | 99 | 1.0:3.0:3.4[b] |
| 7 | Boc-Leu-DAla-DAla-OH (14) | 100 | 12 | 60 | 1.0:5.7:2.5[b] |
| 8a | Boc-Asn(Me$_2$)-DAla-DAla-OH (10) | 100 | 1.5 | 98 | 1.0:14.6:2.8[c] |
| 8b |  | 200 | 1.5 | 99 | 1.0:19.0:6.0[c] |
| 8c |  | 50 | 2 | 97 | 1.0:3.4:1.1[c] |
| 8d |  | 25 | 1.5 | 83 | 1.0:1.9:0.7[c] |
| 9 | Boc-Leu-DAsn(Me$_2$)-DAla-OH (15) | 200 | 12 | 96 | 1.0:8.5:2.7[c] |
| 10 | Boc-Leu-DAla-DAsn(Me$_2$)-OH (16) | 200 | 12 | 85 | 1.0:3.5:1.0[c] |
| 11 | Boc-Asn(Me$_2$)-DAla-DAla-OH (10) | 100 | 1.5 | 16 | 1.0:10.5:0.9[d] |
| 12 | Boc-Leu-DAla-DAsn(Me$_2$)-OH (16) | 100 | 1.5 | 12 | 1.0:3.5:1.6[d] |

[a]Ratios were measured by HPLC at λ = 280 nm.
[b]2.0 equiv of NBP, 250 μL of water, 50 μL of MeOH, 8 μmol of 4.
[c]2.0 equiv of NBP, 1000 μL of water, 200 μL of MeOH, 8 μmol of 4.
[d]50 mol % NBP, 0.033 mmol of 4.

The most striking observation throughout the study was the profound rate acceleration in the presence of peptides containing the N,N-dimethylamide functionality at a particular position. The uncatalyzed reaction delivers essentially equal quantities of 5 and 6 (Table 1, entry 1). N,N-dimethylacetamide itself as a promoter (in various concentrations; entries 2a and 2b) provided neither a noticeable rate acceleration nor a significant change in the 5:6 ratio, although slightly more 8 was observed.

However, when peptides containing the DAla-DAla sequence along with the N,N-dimethylamido side chain were examined, essentially all of the starting material (4) was consumed within 2 h (entries 3-6). These results stand in stark contrast to the rate of consumption of 4 in the control experiments. Moreover, the product distribution responded to structural changes in the peptide. For example, employing peptide 10, with a Asn(Me2)-DAla-DAla structure, 7d-Br derivative 6 was the major product with a 6.8:1 preference over monobromide 5, with the dibromide 8 also formed in considerable quantity (entry 3).

Altering the stereochemistry of the DAsn(Me2) residue (peptide 11; entry 4) also delivered 6 as the major product, but with a lower 6:5 ratio (4.9:1). It was also observed that exchange of the Asn residue to Gln(Me2) (catalyst 12; entry 5) also contributed to efficient consumption of 4, with the dibromide 8 emerging as the dominant product of the reaction. However, this effect was attenuated with the epimeric Gln(Me2) structure 13 (entry 6). When the N,N-dimethylamide moiety was removed from the peptide structure (peptide 14; entry 7), much lower conversion was observed. Even so, in this case a preference for 6 was observed.

The peptide concentration and stoichiometry also appear to influence substantially both the rate and product distribution. Lowering the concentration led to a significant improvement in the 6:5 ratio (14.6:1; entries 3 and 8a) without an appreciable rate decrease. Furthermore, increasing the peptide loading to 200 mol % led to a modest improvement in the 6:5 ratio (19:1; entry 8a vs 8b). On the other hand, lowering the peptide loading to 50 mol % gave a lower 6:5 ratio (3.4:1; entry 8a vs 8c). At 50 mol % peptide, full consumption of 4 was still observed within 2 h. However, reduction of the peptide loading to 25 mol % led to a further erosion of the selectivity relative to the results observed with higher peptide amounts (1.9:1.0; entry 8d). These results imply that while the peptide-based promoters exhibit rate acceleration, a principal hallmark of catalysis, the turnover rates do not appear to be high in the present case. This latter phenomenon may be due to the high affinity of 4 for the DAla-DAla motif. Furthermore, the effect of relocating the Asn(Me2) residue within the tripeptide also appears to influence both the rate and product distribution (cf. entries 8b, 9, and 10). When the residue is disposed closer to the C-terminal position, the peptide appears to be a less effective promoter, as the rate diminishes and the selectivity for 6 decreases. These facts may reveal the importance of situating the putative directing functional group at the right location. Finally, when a limiting quantity (0.5 equiv) of NBP is used, the selectivity trends are preserved and the quantity of dibromide 8 is reduced (entries 11 and 12). The observations in these two experiments suggest that the preference for monobromide 6 is not simply a function of overconversion and depletion of 5.

Figure 3:
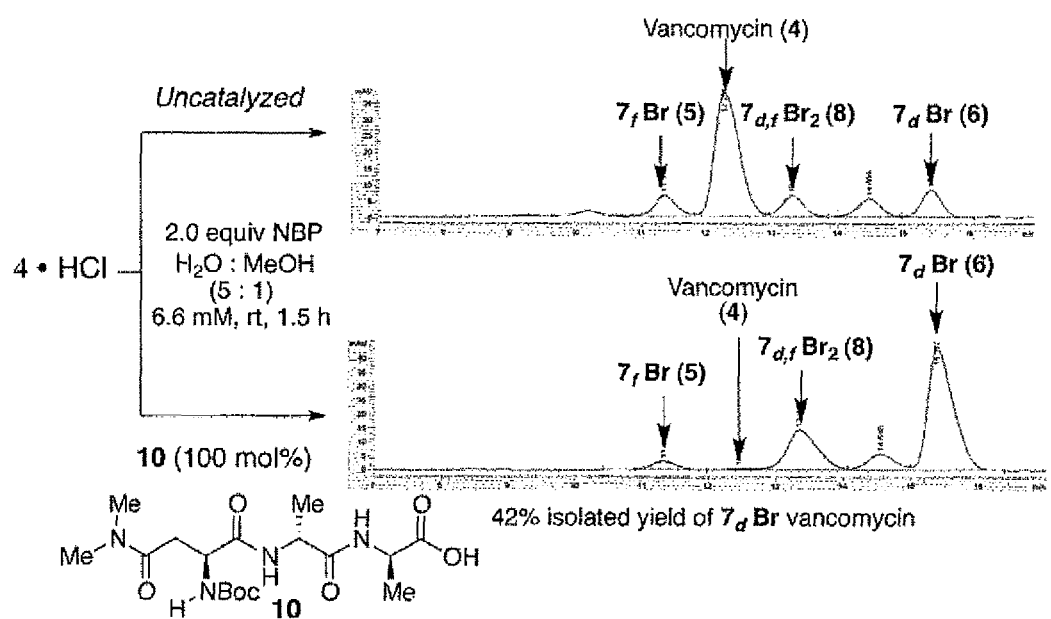
FIG. 3 is an HPLC trace showing the product distribution of uncatalyzed (top) and peptide-catalyzed (bottom, peptide 10) bromination (2.0 eq.) of vancomycin.

Based on the data in Table 1, peptide 10 was selected for further evaluation. Under the optimized reaction conditions, treatment of 100 mg of 4 provided 43.1 mg (41% yield) of analytically pure 7d-Br derivative 6 in a single experiment. By way of comparison, 100 mg of 4 under the uncatalyzed reaction conditions delivered only 11.6 mg (11% yield) of 6, and a quite tedious purification was required. FIG. 3 shows the HPLC traces for the peptide-mediated reaction of 4 with NBP (bottom trace) with that of the corresponding uncatalyzed reaction (top trace) under identical conditions for direct comparison.

The synthesis of dibromovancomycin (8) was also investigated. This particular derivative is generally the major product in the uncatalyzed bromination of 4 with excess brominating reagent. However, as noted, these reactions are generally unselective, which makes product isolation difficult.

Figure 4:
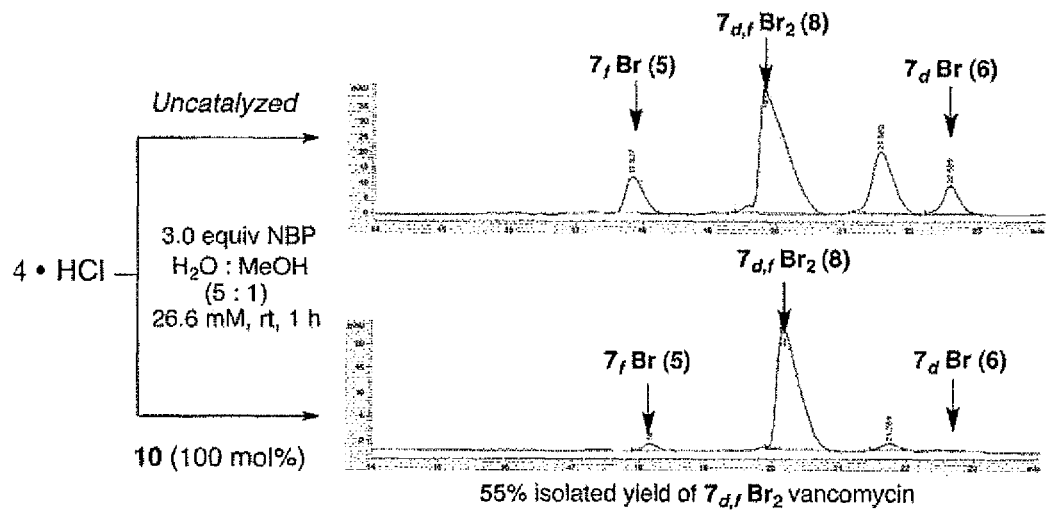
FIG. 4 is an HPLC trace showing the product distribution of uncatalyzed (top) and peptide-catalyzed (bottom, peptide 10) bromination (3.0 eq.) of vancomycin.

On the other hand, treatment of 4 with NBP (3 equiv) in the presence of 100 mol % 10 provides the desired product with excellent efficiency (FIG. 4 bottom). The control reaction provides 8 as a major product, but as a constituent along with significant quantities of the other brominated vancomycins (FIG. 4 top). The treatment of 100 mg of 4 under peptide-promoted reaction conditions provided 60.2 mg (55% yield) of analytically pure 8 in a single experiment.

Figure 5:
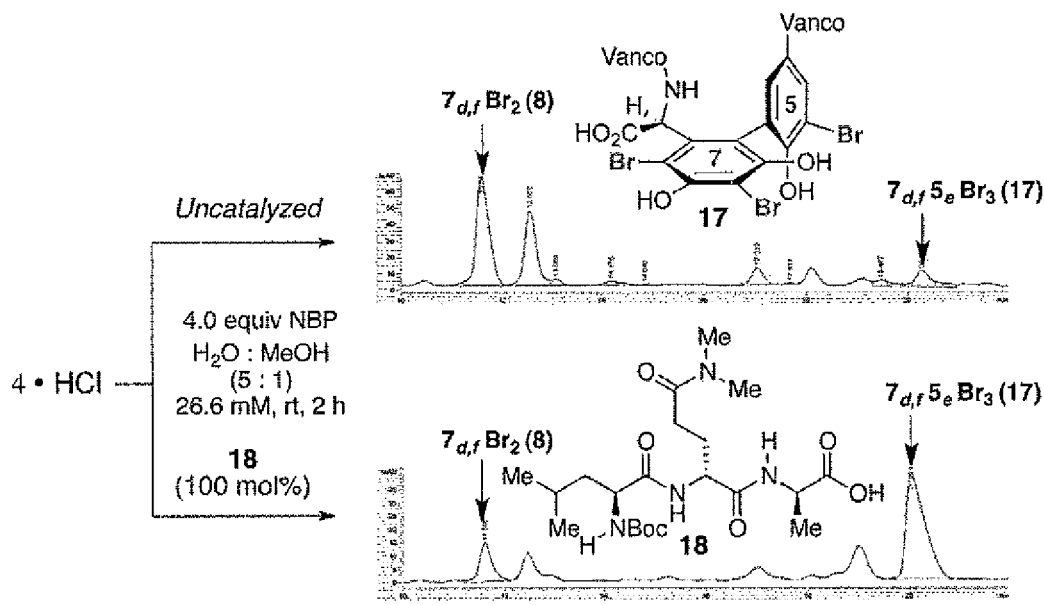
FIG. 5 is an HPLC trace showing the product distribution of uncatalyzed (top) and peptide-catalyzed (bottom, peptide 18) bromination (4.0 eq.) of vancomycin.

Treatment of 4 with NBP in the presence of 100 mol % peptide 10 under otherwise identical conditions resulted in the formation of 8 and 17, although with ratios no better than ~1:1. Compound 17 was identified as the tribromovancomycin, wherein the phenolic moiety of residue 5 was also brominated (FIG. 5). This structural assignment stimulated the exploration of catalyst 18, wherein the central Gln(Me2) residue was postulated to place the dimethylamido moiety in proximity to this previously recalcitrant bromination site. When 4 was exposed to NBP under the reaction conditions in the presence of catalyst 18, tribromide 17 was produced in significant quantity preferentially over the dibromide (17:8=3-4:1; FIG. 7 bottom) in a substantially cleaner reaction. This observation demonstrates the power of a peptide catalyst to provide a new brominated vancomycin that is otherwise difficult to acquire. In a preparative mode, 49.0 mg of 4 led to the isolation of 20.2 mg (35% yield) of 17.

The reversal of the selectivity exhibited by peptide 10, which preferentially delivers monobromide 6, was also investigated. A preliminary examination of DAla-DAla-based peptides did not unveil a 5-selective catalyst.

Figure 2:
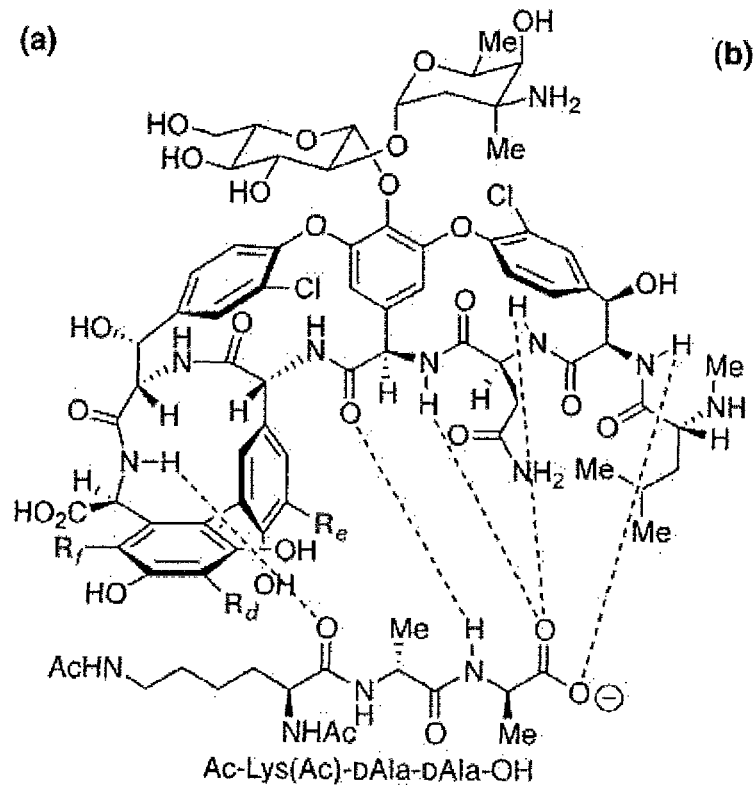
FIG. 2 is a representation of the binding of vancomycin to Ac-Lys(Ac)-DAla-DAla-OH segments of the bacterial cell wall.

However, in the course of these studies, we made the surprising observation that the reaction medium had a substantial effect on the site-selectivity of the initial bromination. When 4 was exposed to 2 equiv of NBP in either H2O:MeOH (5:1) or MeOH alone, sluggish reactions occur, and the ratio of 5:6 is near unity (Table 2, entries 1 and 2).

of 4 with 4 equiv of NBP in the presence of guanidine provided 23.3 mg (21% yield) of analytically pure 5, which is otherwise very difficult to isolate cleanly in significant quantities (FIG. 2). These results are consistent with the hypothesis that guanidine may associate with the acid of 4 and simultaneously deliver the bromide ion. This effect may lead to kinetically favored formation of 5 and also the formation of 8 via depletion of 6.

Example 2. Halogenation of Teicoplanin

Figure 6:
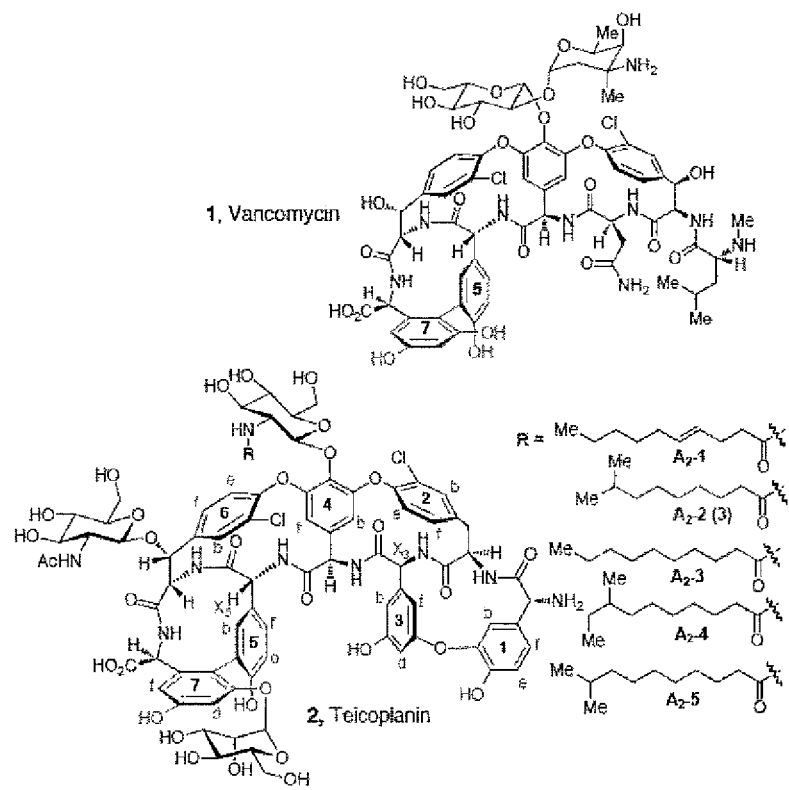
FIG. 6 is a representation comparing the structures of vancomycin and teicoplanin, including identification of the 1,3-biaryl group and the 5,7-biaryl group. The protons on the 7-aryl ring are designated $7_f$ and $7_d$. The protons on the 5-aryl ring are designated $5_b$, $5_e$ and $5_f$. The protons on the 1-aryl ring are designated $1_b$, $1_e$ and $1_f$. The protons on the 3-aryl ring are designated $3_b$, $3_d$, and $3_f$.

The structures of vancomycin and teicoplanin are shown in FIG. 6. Given the heightened biological activity and higher level of molecular complexity of teicoplanin compared to vancomycin, site-selective halogenation of teicoplanin was investigated. The structure of teicoplanin presents the additional challenge of tuning the site of bromination to either the 5,7-biaryl region of the structure (2, FIG. 6, rings 5 and 7) or the 1,3-biaryl-ether region (2, FIG. 6, rings 1 and 3). The intrinsic reactivity of these moieties, relative to one another, was not completely clear at the outset. Thus, one of the key goals of the study was to evaluate catalysts/conditions that could provide site-selective bromination of either biaryl ring system. Teicoplanin was purified to isolate teicoplanin A2-2 (3, FIG. 6) from the readily available mixture of teicoplanins, which is a composite of approximately six to nine molecular forms of teicoplanin.

Halogenation in the Absence of Peptide Catalyst

Figures 7A, 7B, 7C, 7D, 7E:
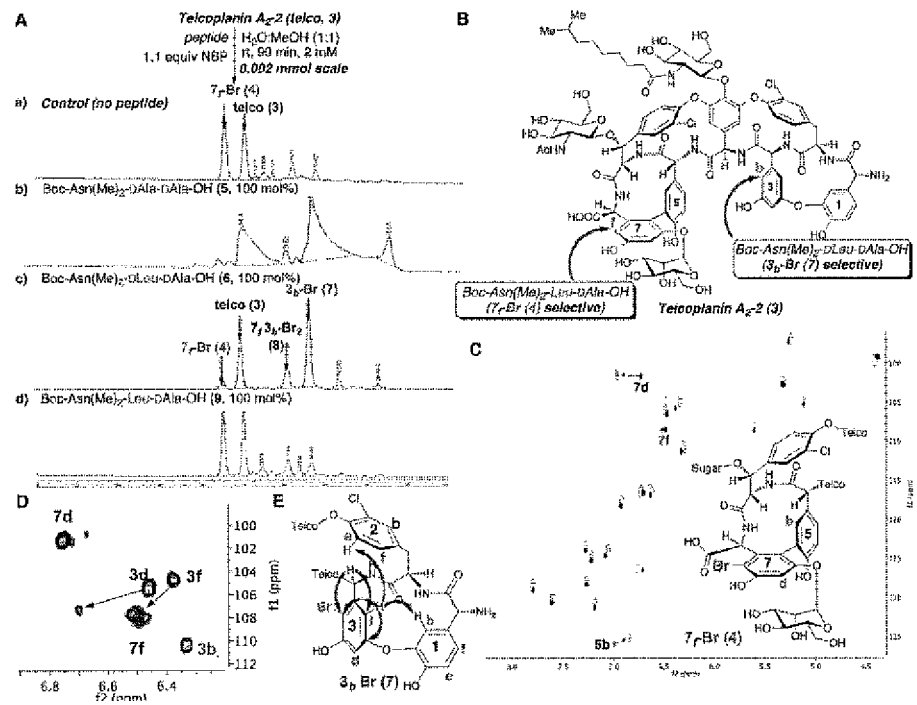
FIG. 7A (a)-(d) is a series of HPLC traces showing the product distribution of the uncatalyzed bromination of teicoplanin (a) and the bromination in the presence of peptides 5 (b), 6 (c), and 9 (e).
FIG. 7B is the structure of the brominated analogs 4 and 7.
FIG. 7C is an overlay of the HSQC spectrum of 4 (light colored dots) with 3 (dark colored dots).
FIG. 7D is an overlay of the HSQC spectrum of 7 (light colored dots) with 3 (dark colored dots).
FIG. 7E is a NOESY correlation supportive of the structural assignment of 7.

As shown in FIG. 7A, when teicoplanin (3) was dissolved in MeOH/H2O (1:1) and reacted with 1 equiv of NBP, a

TABLE 2

Optimization of the Reaction Conditions Aiming at Analogue 5[a]

| Entry | Additive | Solvent | NBP (equiv) | t (h) | % conv. | 5 6 8 $7_fBr:7_dBr:7_{d1}Br_2$ |
|---|---|---|---|---|---|---|
| 1 | No catalyst | H₂O:MeOH (5:1) | 2 | 12 | 71 | 1.0:1.0:1.3[b] |
| 2 | No catalyst | MeOH | 2 | 2 | 17 | 1.0:1.0:3.0[b] |
| 3 | No catalyst | MeOH | 4 | 1 | 92 | 14.3:1.0:53.8[c] |
| 4 | 10 | MeOH | 4 | 1 | 31 | 0.5:1.0:1.3[b] |
| 5 | Guanidine•HCl | MeOH | 4 | 1 | 85 | 12.7:1.0:10.8[c] |
| 6 | Guanidine•HCl | MeOH | 4 | 1 | 92 | 11.8:1.0:11.4[d] |

[a]Ratios were measured by HPLC at λ = 280 nm.
[b]8 μmol of 4, 6.6 mM.
[c]16 μmol of 4, 3.3 mM, 18 equiv of guanidine•HCl.
[d]similar to (c) except with 6 equiv of guanidine•HCl.

Yet, when a larger quantity (4 equiv of NBP) was used, in the absence of a catalyst, a surprising preference for 5 is observed, with a substantial increase in the observed quantity of dibromide 8 (entry 3). Peptide 10 maintains its capacity to favor 6 in MeOH solvent, although the selectivity is strongly attenuated (entry 4).

Finally, guanidine was investigated as an additive because of its propensity to accelerate bromination reactions. Additionally, guanidine possesses the capacity to bind carboxylate under a variety of conditions. Thus, it was hypothesized that guanidine might effectively target the acid of 4 while simultaneously delivering bromide to the proximal 7f site of 4. As illustrated in entries 5 and 6, guanidine not only provides 5 with good selectivity over 6 but also significantly improves the ratio of monobromide (5) to dibromide (8), making viable the isolation of 5 in good quantities (entry 3 vs 5 and 6). On a preparative scale, the reaction of 100 mg major product was observed, with unreacted 3 also prominent in the HPLC trace (FIG. 2A(a)). When multiple equivalents were employed, a highly complex mixture of products was observed. The reaction with 1 equiv allowed for isolation and purification of the major brominated species (4; FIG. 2B). On a preparative scale, 50.0 mg of 3 could be converted to 10.0 mg of analytically pure 4 with 6.0 mg of recovered 3 in a single operation. LC-MS analysis revealed that the new compound was a mono-brominated form of teicoplanin A2-2. FIG. 2C shows an overlay of a diagnostic region of the HSQC spectrum for both 3 and 4. Most notably, the cross peak that was assigned to the ring 7f (C—H) correlation is absent in 4. At the same time, there is excellent overlay of the overwhelming majority of the other peaks, suggesting a minimum structural alteration. The cross peak for the 7d and 5b (C—H) correlation has shifted slightly, as highlighted in FIG. 2C, suggesting substitution within the 5,7-biaryl substructure. Additional data also supports the assignment of 4 as the ring 7f-Br variant of teicoplanin A2-2.

Halogenation in the Presence of Peptide Catalysts

Teicoplanin was initially reacted with catalysts like 5, as described above for vancomycin, designed to mimic the binding of vancomycin and teicoplanin to their biological target, but outfitted with functional groups that might accelerate brominaton. When 3 was exposed to bromination conditions in the presence of peptide 5, bromination was observed, but the analytical HPLC trace exhibited broad peaks, as shown in FIG. 7A(b). The peak shape renders analysis of reaction mixture and isolation of pure materials difficult. The peak shapes were attributed to the formation of robust (i.e., too robust) 3-peptide complexes. This assertion is consistent with the known, very high affinity of 3 for DAla-DAla-based peptides (Ka=1.6×106 for Ac-Lys-DAla-DAla at pH=5.0).

In an attempt to overcome the formation of these complexes, one of the DAla units was replaced with a DLeu. The corresponding bromination of 3 with Boc-Asn(Me)2-DLeu-DAla-OH (6) as a promoter of the reaction produces a reaction mixture that was readily analyzed by HPLC/LC-MS (FIG. 8A(c)). Strikingly, peptide 6 diverts the reaction to give a new monobrominated teicoplanin, which was not observed in significant quantities in the absence of 6. As detailed below, the structure of the new, 6-dependent monobrominated teicoplanin may be assigned as the ring 3b-Br analog 7. The capacity of peptide 6 to re-direct the site of bromination away from the intrinsically more reactive 5,7-ring system to the less reactive 1,3-ring system is a manifestation of nonenzymatic control of site-selectivity in a highly complex molecular environment. The reaction specificity is also highly dependent on peptide structure and stereochemistry. Alteration of the configuration of the DLeu residue of the peptide to the L-configuration, as in 9 (Boc-Asn(Me)2-Leu-DAla-OH), produced a very different result (FIG. 7A(d)). In this case, the major product was reverted to 7f-Br compound 4. Presumably, these results are due to the reduced binding affinity of the stereochemically mismatched peptide 9 to 3 during the bromine transfer reaction. On preparative scale, in the presence of peptide 10, 160.0 mg of 3 provided 47.0 mg of analytically pure 7 (with 35.0 mg of recovered 3) in a single step. The assignment of the structure for 7 was confirmed by NMR experiments.

Figures 8A, 8B, 8C:
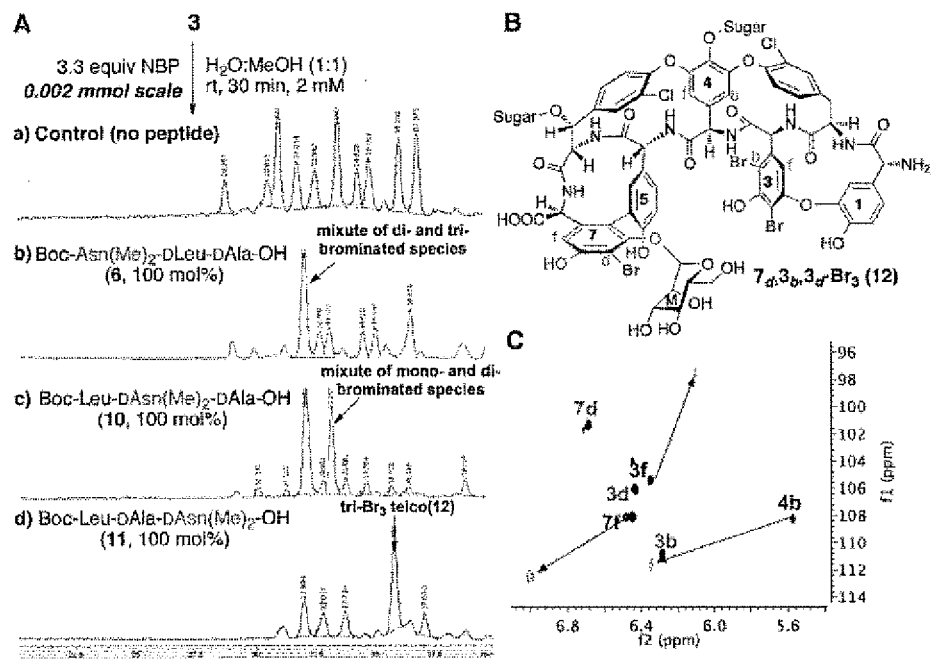
FIG. 8A is an HPLC trace showing the effect of peptide on the site-selectivity of teicoplanin tribromination compared to the control reaction.
FIG. 8B is the assigned structure of the tribrominated teicoplanin.
FIG. 8C is an overlay of the HSQC spectrum of 12 (light colored dots) with 3 (dark colored dots).

Pronounced peptide-dependent effects were also observed in the bromination of teicoplanin A2-2. As shown in FIG. 8A, when 3 was exposed to an excess of NBP (3.3 equiv), either in the absence or in the presence of different peptides (6, 10 and 11, with variable location of the Asn(Me)2 side chain) different product distributions were obtained. In the absence of a peptide-based promoter, a highly complex mixture of products was obtained (FIG. 8A(a)). One implication is that there appears to be a comparable level of reactivity for many sites within teicoplanin A2-2 as further functionalization occurs. Even so, the reaction mixtures are substantially less complex when peptide-based promoters were evaluated (FIG. 8A(b)-(d)), exhibiting their capacity to perturb site-selectivity among the less reactive sites. When a peptide bearing the N-terminal Asn(Me)2 side chain was employed (6), the reaction mixture contains a number of products, including a prominent HPLC peak that contains an inseparable mixture of di- and tribromides (FIG. 8A(b)). When the Asn(Me)2 is central to the tripeptide (10), two peaks were observed in the HPLC trace that once again contain mixtures (FIG. 8A(c)). Yet, when the Asn(Me)2 is in the C-terminal position (11), a striking, peptide-dependent outcome was observed, with a new, homogeneous peaks apparent in the HPLC trace (FIG. 8A(d)). LC-MS analysis reveals the compound to be a new tribrominated species. NMR analysis identified the compound as 7d,3b,3d-Br3 teicoplanin analog (12, FIG. 8). On a preparative scale, 15 mg of 12 was obtained from 80 mg of 3 in a single operation.

Metal-Catalyzed Suzuki Cross-Coupling Reactions of Brominated Teicoplanin

Figures 9A, 9B, 9C:
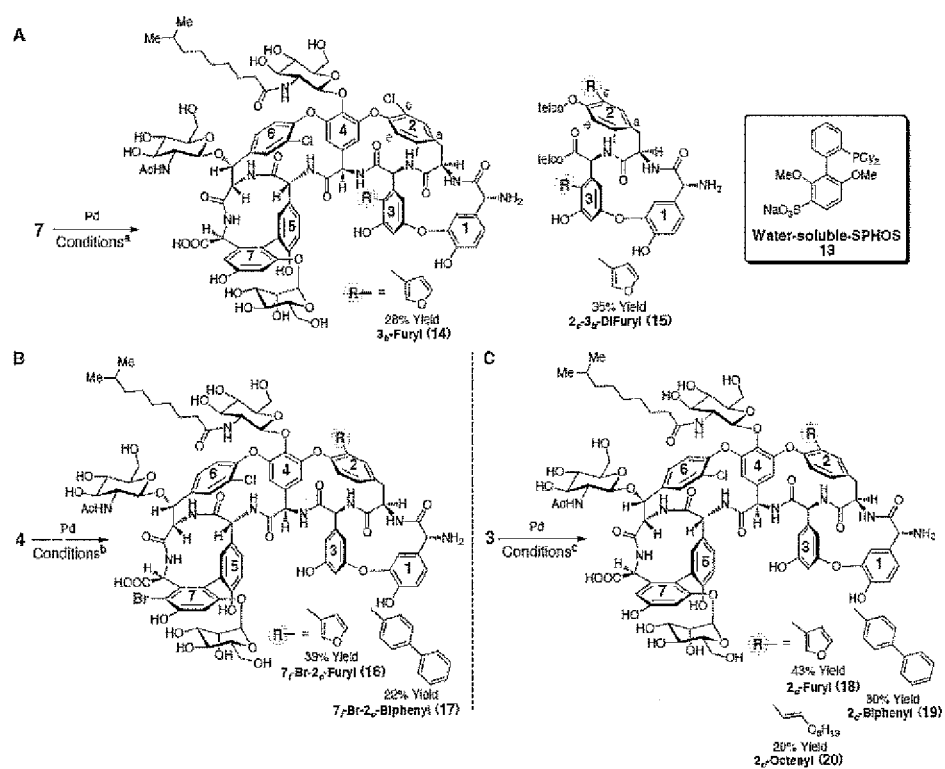
FIG. 9A is a reaction scheme for the cross-coupling of compound 7; Conditions: $^a$50 mol % Pd(OAc)$_2$, 100 mol % Water-soluble-SPHOS, K$_2$CO$_3$ (10 equiv), Boronic acid (10 equiv), H$_2$O:MeCN (2:1), 35° C. for 14 and 50° C. for 15. B) Crosscoupling of compounds 4. $^b$50 mol % Pd(OAc)$_2$, 100 mol % Water-soluble-SPHOS, K$_2$CO$_3$ (10 equiv), Boronic acid (10 equiv), H$_2$O:MeCN (2:1), 35° C. 16 and 50° C. for 17. C) Cross-coupling of compounds 3. $^c$100 mol % Pd(OAc)$_2$, 100 mol % Water-soluble-SPHOS, K$_2$CO$_3$ (10 equiv), Boronic acid (10 equiv), H$_2$O:MeCN (2:1), 50° C.
Figure 10:
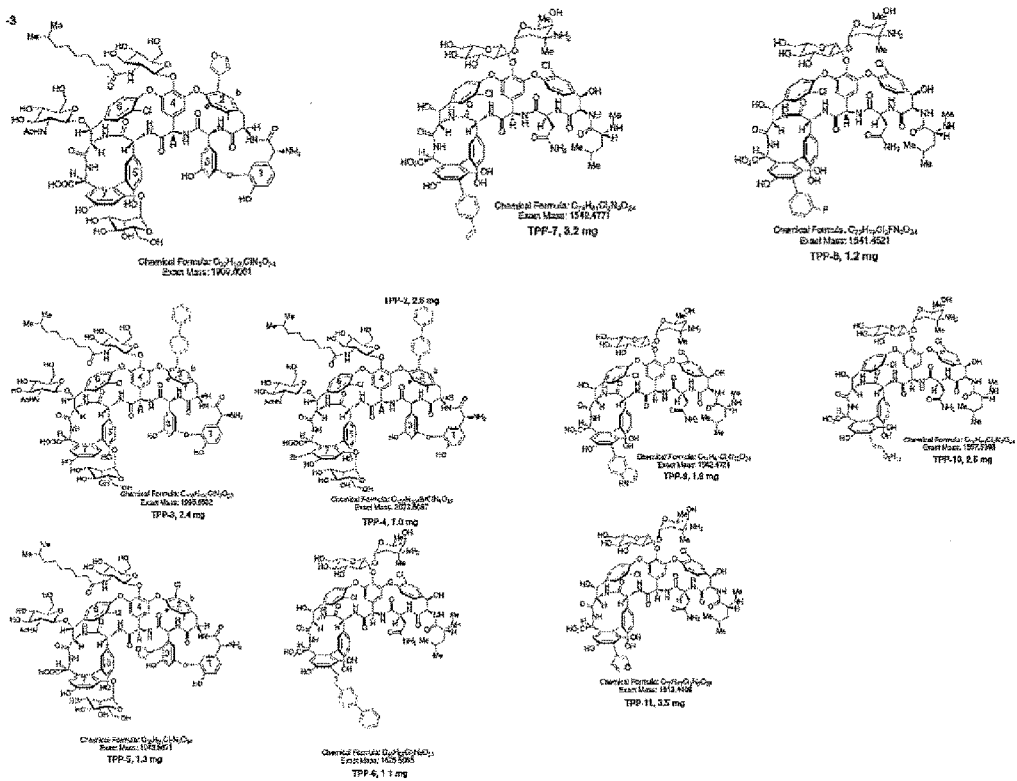
FIG. 10 shows the structures of the compounds that have been prepared using the methods described herein.
Figure 10:
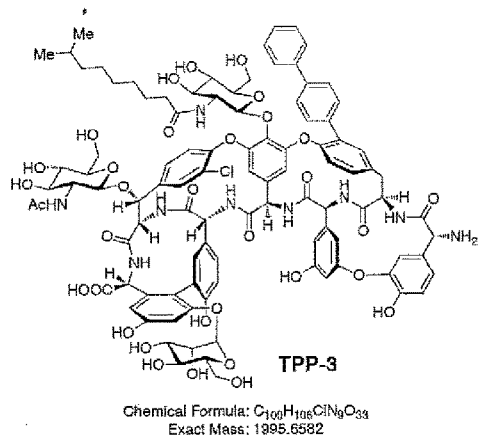
Figure 10:
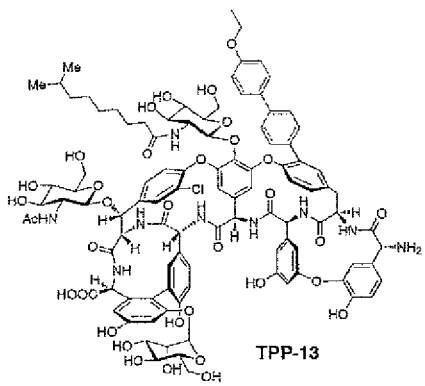
Figure 10:
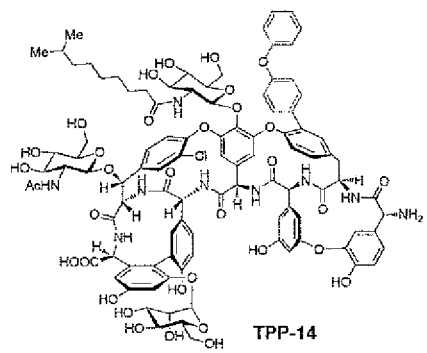
Figure 10:
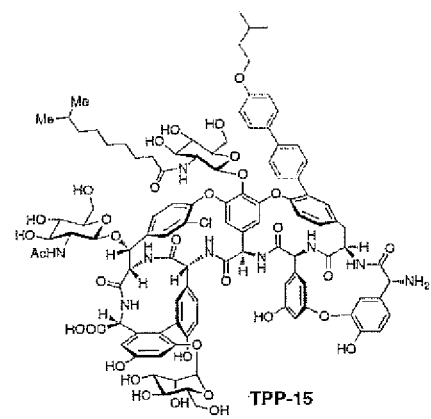
Figure 10:
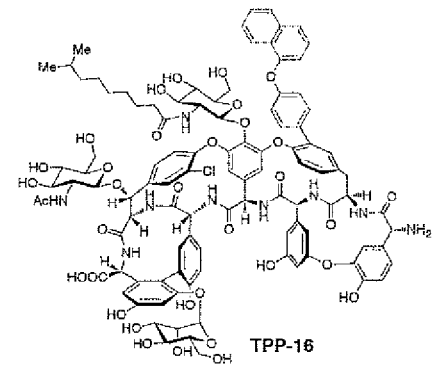
Figure 10:
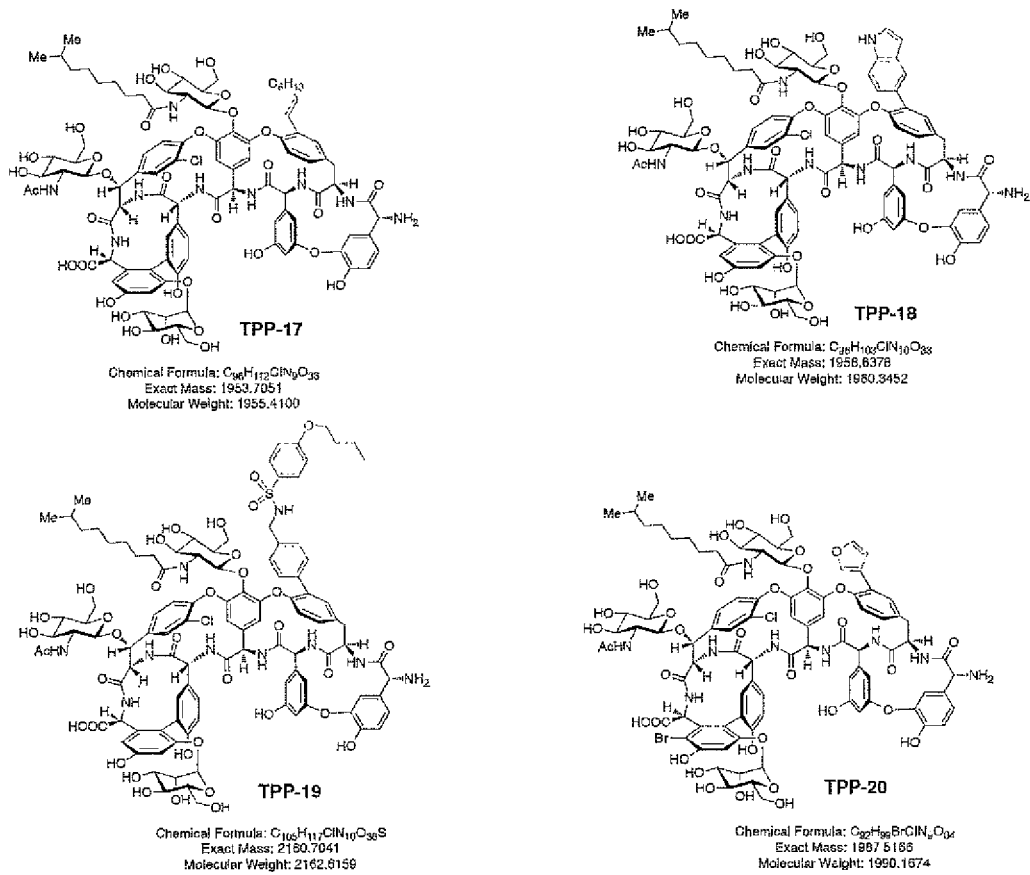
Figure 10:
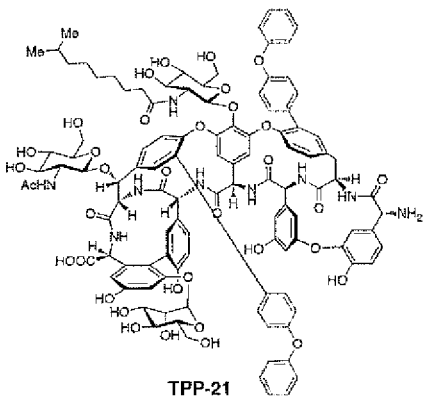
Figure 10:
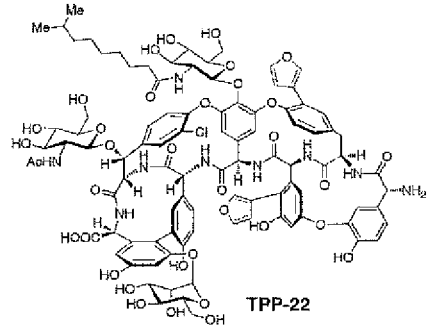
Figure 10:
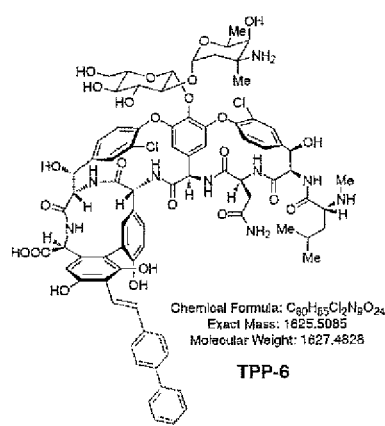
Figure 10:
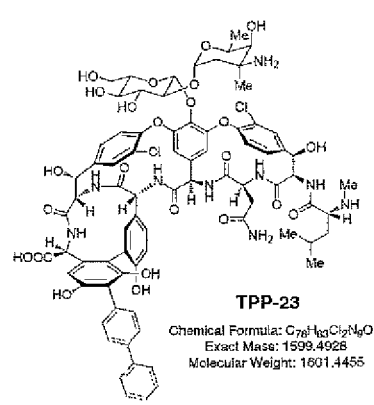
Figure 10:
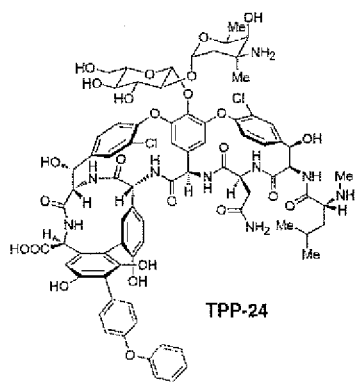
Figure 10:
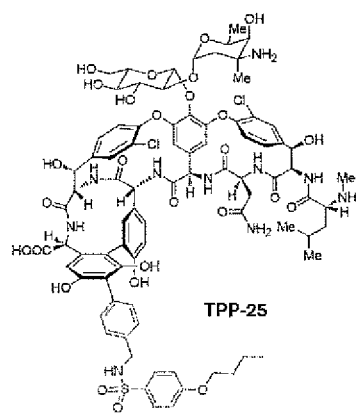
Figure 11:
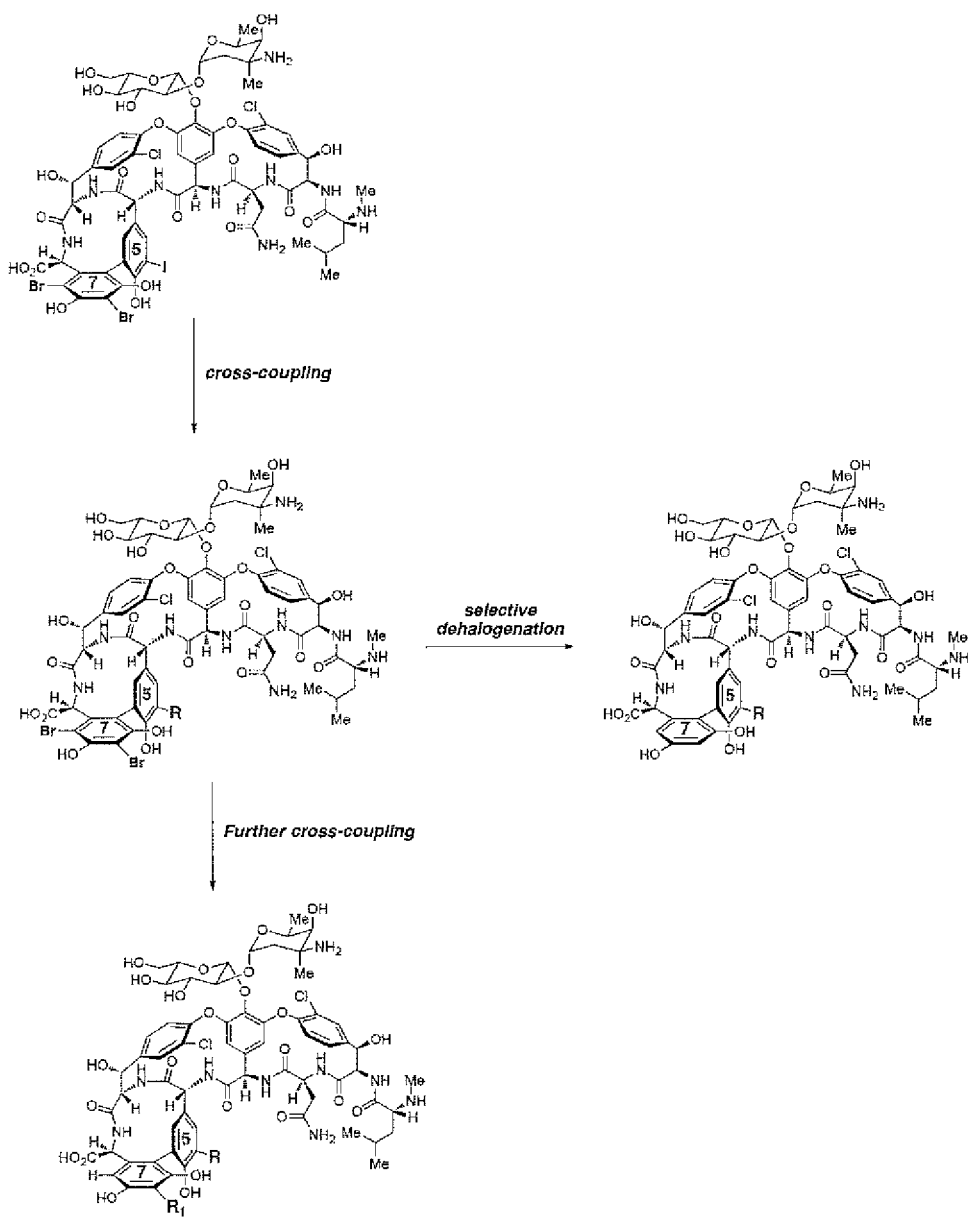
FIG. 11 is a scheme showing a methodology for functionalizing glycopeptide antibiotics after cross-coupling.

The brominated variants of 3 were investigated as substrates for metal-catalyzed Suzuki cross-coupling reactions. Poor results were initially obtained due to the apparent binding of Pd reagents to teicoplanin that resulted in inhibition of catalysis. However, the use of higher loadings of Pd (50 mol %) along with the water-soluble phosphine ligand 13 (100 mol %) allowed cross-coupling to occur with useful efficiencies. For example, when bromoteicoplanin 7 was subjected to these conditions, furan-containing teicoplanin analog 14 was obtained in 28% yield, in a single step, with high purity after reverse phase HPLC purification (FIG. 9A). Analysis of the reaction mixture prior to purification by LC-MS revealed the presence of a minor, doubly functionalized product with two furyl groups, and possessing only a chlorine atom, suggesting functionalization of one of the indigenous chlorines of 3. This compound was assigned as 15, and was isolated in 35% yield under conditions optimized for its formation. Bromo-teicoplanin 4, under analogous conditions, may be converted to compound 16 or 17, where substitution of the typically less reactive (towards metal-catalyzed cross-coupling) C—Cl bond has occurred, rather than at the generally more reactive C—Br bond (FIG. 4B). The unexpected high reactivity of the ring 2c position of 3 was the basis for the investigation of the Pd-catalyzed cross coupling of native 3 under related conditions. Compounds 18, 19 and 20 were obtained in 43%, 30% and 20% isolated yield, respectively (FIG. 9C). FIG. 10 shows the chemical structure of compounds prepared using the methods described herein. FIG. 11 shows a methodology for functionalizing glycopeptide antibiotics after cross-coupling.

Determination of In Vitro Antibiotic Activity

The chemistry described above enabled direct synthesis of eleven previously unknown analogs of 3. The minimum inhibitory concentrations (MICs) for the new analogs as antibacterial agents as determined. The compounds against five bacterial strains, including methicillin-resistant *S. aureus* (MRSA) and vancomycinresistant *enterococcus* (VRE; VanB exhibits vancomycin resistance, but it is teicoplanin susceptible; VanA is both vancomycin and teicoplanin resistant). The results are shown in Table 3.

TABLE 3

Minimum inhibitory concentrations of glycopeptide antiobiotic analogs

| Entry | Compound | MSSA$^{a,b}$ | MRSA$^c$ | VSE$^d$ | VRE (VanB)$^e$ | VRE (VanA)$^f$ |
|---|---|---|---|---|---|---|
| 1 | Vancomycin | 0.5 | 1 | 2 | 16 | >64 |
| 2 | Teicoplanin | 0.5 | 0.5 | 0.25 | 0.25 | >64 |
| 3 | Teicoplanin A$_2$-2 | 0.5 | 0.5 | 0.25 | 0.25 | >64 |
| 4 | 4 | 0.5 | 1 | 0.5 | 1 | >64 |
| 5 | 7 | 0.5 | 1 | 0.25 | 0.5 | >64 |
| 6 | 8 | 1 | 1 | 0.5 | 1 | >64 |
| 7 | 12 | 2 | 2 | 4 | 8 | >64 |
| 8 | 14 | 0.25 | 0.25 | 0.25 | 0.5 | >64 |
| 9 | 18 | 0.25 | 0.25 | 0.12 | 0.12 | 32 |
| 10 | 15 | 0.25 | 0.25 | 0.12 | 0.25 | >32 |
| 11 | 16 | 0.5 | 0.5 | 0.25 | 0.5 | >64 |

TABLE 3-continued

Minimum inhibitory concentrations of glycopeptide antiobiotic analogs

| Entry | Compound | MSSA[a,b] | MRSA[c] | VSE[d] | VRE (VanB)[e] | VRE (VanA)[f] |
|---|---|---|---|---|---|---|
| 12 | 17 | 4 | 2 | 1 | 0.5 | 32 |
| 13 | 19 | 8 | 4 | 0.5 | 0.25 | 8 |
| 14 | 20 | 8 | 4 | 0.5 | 0.25 | 1 |
| 15 | Linezolid | 4 | 4 | 2 | 2 | 2 |

[a]MIC values reported in µg/mL.
[b]MSSA = methicillin-susceptible *S. aureus*, ATCC 29213.
[c]MRSA = methicillin-resistant *S. aureus*, ATCC 43300.
[d]VSE = vancomycin-susceptible enterococci, ATCC 29212.
[e]VRE = vancomycin-resistant enterococci, ATCC 51299.
[f]MMX 486. See Supporting Information for additional details.

As shown in Table 3, in comparison to control compounds (entry 1-3), the newly synthesized analogs 4, 7 and 8 (entries 4-6) are quite similar in potency to 3 against all five bacterial strains. In contrast, tribrominated teicoplanin A2-2 (12, entry 7) exhibits a decrease in activity with four of the five strains. On the other hand, the analogs obtained through cross-coupling (entries 8-13) demonstrated comparable or increased potency against several of the bacterial strains, in comparison to vancomycin and teicoplanin. Compound 14, for example, with furyl substitution at the 3b-position, exhibited higher potency against the MRSA strain (entries 1-3 vs. 8). Relocation of furyl substituent from the 3b-position to the 2c position (compound 18, entry 9) resulted in enhancement of activity against VRE strains (entries 1-3 vs. 9). Compound 15 (entry 10), with both 2c- and 3b-positions substituted with a furyl group, exhibits a similar activity profile in comparison to 14 and 18 (entry 8 and 9). Compound 16 (entry 11) possessing the 7f-bromine substituent and the 2c-furyl group also maintains an analogous profile. A striking and different profile was observed with compounds 17, 19 and 20 (entries 12-14). Substitution of the 2c-position of 3 with biphenyl functionality (compound 19) resulted in significant activity against VRE (VanA) strain. Simultaneously, however, compound 19 exhibits a loss of potency when evaluated against MSSA and MRSA strains. Compound 17 (entry 12), with a 7f-Br and a 2c-biphenyl functionality, also exhibits this trend. Compound 20, with ring 2c-octenyl substitution, exhibits the trend as well, while showing quite high (significant) potency against both vancomcin- and teicoplanin-resistant strain (Van A, entries 1-3 vs. 14). These data are compared to antibacterial behaviors of the antibiotic Linezolid in entry 15. The unique behaviors of biphenyl-containing compounds 17, 19 and 20 may suggest change in the mechanism of action. The data presented in Table 1 demonstrate that altering the structure of teicoplanin with either bromination, or cross-coupling reactions of either brominated teicoplanins (4 and 7) or teicoplanin A2-2, itself (3), can lead to compounds with significant anti-bacterial activity against strains that exhibit vancomycin and teicoplanin resistance.

We claim:

1. A compound of Formula II:

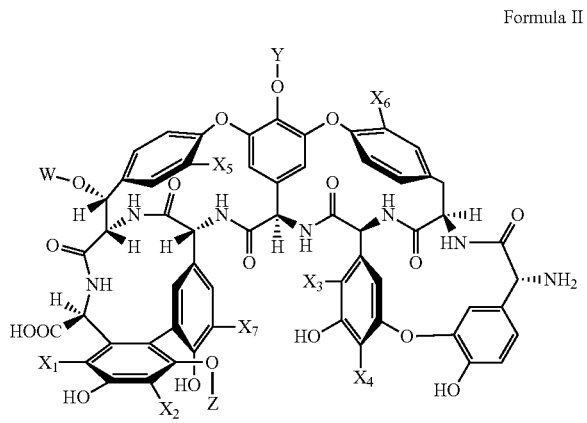

Formula II wherein:
each of $X_1$-$X_4$ and $X_7$ is independently selected from the group consisting of hydrogen, Br, Cl, I, alkyl, substituted alkyl, cycloalkyl, substituted cycloalkyl, heterocycloalkyl, substituted heterocycloalkyl, alkenyl, substituted alkenyl, alkynyl, substituted alkynyl, aryl, substituted aryl, heteroaryl, substituted heteroaryl, amino, primary amine, or secondary, amine, alkoxy, thioether, formyl, acyl, or carboxylic acid, wherein at least one of $X_1$-$X_4$ is not hydrogen, $X_5$ and $X_6$ are independent selected from the group consisting of hydrogen, Br, Cl, I, alkyl, substituted alkyl, cycloalkyl, substituted cycloalkyl, heterocycloalkyl, substituted heterocycloalkyl, alkenyl, substituted alkenyl, alkynyl, substituted alkynyl, aryl, substituted aryl, heteroaryl, substituted heteroaryl, amino, primary amine, or secondary, amine, alkoxy, thioether, formyl, acyl, or carboxylic acid, W, Y, and Z are independently selected from the group consisting of hydrogen, alkyl, substituted alkyl, aryl, substituted aryl, heteroaryl, substituted heteroaryl, and carbohydrate, wherein if the compound is ristocetin and $X_3$ is I, then $X_1$ and/or $X_2$ are other than hydrogen and/or $X_5$ and/or $X_6$ are other than chlorine, and wherein $X_3$ and/or $X_6$ is aryl or wherein $X_3$ and/or $X_6$ is alkenyl.

2. The compound of claim 1, wherein W is hydrogen or N-acetylglucosamine.

3. The compound of claim 1, wherein Z is hydrogen or alpha-D-mannose.

4. The compound of claim 1, wherein Y is hydrogen or a substituted beta-D-glucosamine having the structure:

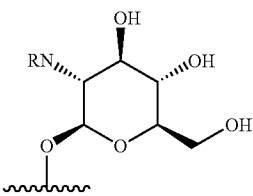

wherein R is an acyl (R—(C═O)—) group.

5. The compound of 10, wherein R is selected from the group consisting of 4-decenoyl ($A_{2\text{-}1}$), 9-methylnonanoyl ($A_2$-2), decanoyl ($A_2$-3), 8-methyldecanoyl ($A_2$-4), 9-methyldecanoyl ($A_2$-5).

6. The compound of claim 1, wherein $X_1$ is Br, Cl, or I.

7. The compound of claim 1, wherein $X_2$ is Br, Cl, or I.

8. The compound of claim 1, wherein $X_3$ is Br, Cl, or I.

9. The compound of claim 1, wherein $X_4$ is Br, Cl, or I.

10. The compound of claim 1, wherein $X_7$ is Br, Cl, or I.

11. The compound of claim 1, wherein $X_3$ and/or $X_6$ is 3-furyl.

12. The compound of claim 11, wherein $X_1$, $X_2$, and $X_4$ are hydrogen, $X_3$ is 3-furyl, and $X_5$ and $X_6$ are chlorine.

13. The compound of claim 11, wherein $X_1$, $X_2$, and $X_4$ are hydrogen, $X_3$ and $X_6$ is 3-furyl, and $X_5$ is chlorine.

14. The compound of claim 11, wherein $X_1$ is Br, $X_2$-$X_4$ are hydrogen, $X_5$ is Cl, and $X_6$ is 3-furyl.

15. The compound of claim 1, wherein $X_1$ is Br, $X_2$-$X_4$ are hydrogen, $X_5$ is Cl, and $X_6$ is biphenyl.

16. The compound of claim 1, wherein $X_1$-$X_4$ are hydrogen, $X_5$ is Cl, and $X_6$ is biphenyl.

17. The compound of claim 1, wherein $X_1$-$X_4$ are hydrogen, $X_5$ is Cl, and $X_6$ is 1-octenyl.

18. A pharmaceutical composition comprising an effective amount of one or more compounds of claim 1 and one or more pharmaceutically acceptable carriers.

19. A method of treating a bacterial infection, the method comprising administering the composition of claim 18 to an individual in need thereof.

20. The method of claim 18, wherein the bacterial infection is selected from the group consisting of methicillin-susceptible *S. aureus* (MSSA), methicillin-resistant *S. aureus* (MRSA), vancomycin-sensitive enterococci (VSE), vancomycin-resistant enterococci (VRE), vancomycin-resistant *S. aureus* (VRSA), or combinations thereof.

21. The method of claim 18, wherein the composition is administered parenterally or orally.

* * * * *